US005869665A

United States Patent [19]

Padia

[11] Patent Number: 5,869,665
[45] Date of Patent: Feb. 9, 1999

[54] QUINAZOLINONE DERIVATIVES AS CHOLECYSTOKININ (CCK) LIGANDS

[75] Inventor: Janak Khimchand Padia, Ypsilanti, Mich.

[73] Assignee: Warner-Lambert Company, Morris Plains, N.J.

[21] Appl. No.: 826,843

[22] Filed: Apr. 8, 1997

Related U.S. Application Data

[60] Division of Ser. No. 500,436, Jul. 10, 1995, Pat. No. 5,756,502, which is a continuation-in-part of Ser. No. 287,454, Aug. 8, 1994, abandoned.

[51] Int. Cl.$^6$ .................. A61K 31/50; A61K 31/505; C07D 239/88; C07D 239/93
[52] U.S. Cl. .................. 544/236; 544/256; 544/257; 544/259; 544/260; 544/258; 544/280; 544/284; 544/287; 514/248; 514/249; 514/258; 514/259; 514/260
[58] Field of Search ............................ 544/236, 256, 544/257, 258, 259, 260, 280, 284, 287

[56] References Cited

U.S. PATENT DOCUMENTS

| 3,213,094 | 10/1965 | Morgan et al. | 514/259 |
|---|---|---|---|
| 3,217,005 | 11/1965 | Kirchner et al. | 514/259 |
| 3,322,766 | 5/1967 | Schipper | 514/259 |
| 3,867,384 | 2/1975 | Bullock et al. | 514/259 |
| 4,276,295 | 6/1981 | Ishikawa et al. | 424/251 |
| 4,472,400 | 9/1984 | Tully et al. | 514/259 |
| 4,668,682 | 5/1987 | Sekiya et al. | 514/259 |
| 5,084,457 | 1/1992 | Fanshawe et al. | 514/259 |
| 5,196,427 | 3/1993 | Yu et al. | 514/259 |
| 5,204,354 | 4/1993 | Chakravarty et al. | 514/259 |
| 5,278,316 | 1/1994 | Horwell et al. | 514/259 |
| 5,342,944 | 8/1994 | Mohan et al. | 544/284 |

FOREIGN PATENT DOCUMENTS

| 139715 | 1/1980 | Germany . |
|---|---|---|
| 158549 | 1/1983 | Germany . |
| 213214A | 1/1983 | Germany . |
| 234671A | 2/1985 | Germany . |
| 225131A1 | 7/1985 | Germany . |
| 1038729 | 6/1965 | United Kingdom . |
| 1038729 | 8/1966 | United Kingdom . |
| 2086903 | 11/1981 | United Kingdom . |
| WO9113907 | 9/1991 | WIPO . |
| WO9320055 | 3/1992 | WIPO . |
| WO9403447 | 2/1994 | WIPO . |

OTHER PUBLICATIONS

16128u, *Chemical Abstracts*, vol. 78, 1973.
87715d, *Chemical Abstracts*, vol. 70, 1969.
140064s, *Chemical Abstracts*, vol. 82, 1975.
105:97416n, *Chemical Abstracts*, vol. 105, 1986.
96:142790p, *Chemical Abstracts*, vol. 96, 1982.
85:123860t, *Chemical Abstracts*, vol. 85, 1976.
"Intracerebroventricular Injections of Cholecystokinin Octapeptide Suppress Feeding, etc.", *Regulatory Peptides*, R.R. Schick, et al, 14 (1986) 277–291.

"Antinociceptive Action of Cholecystokinin Octapeptide, etc.", *Neuropharmacology*, R.G. Hill, et al, vol. 26, No. 4, pp. 289–300, 1986.
"Inhibition of Synaptic Transmission in the Hippocampus, etc.", *Brain Research*, Brian A. MacVicar, et al, 406 (1987) 130–135.
"Peptides, The Limbic Lobe and Schizophrenia", Gareth W. Roberts, et al, *Brain Research*, 288 (1983) 199–211.
"Cholecystokinin–Immunoreactive Boutons in Synaptic Contact, etc.", S.Totterdell and A.D. Smith, *Neuroscience*, vol. 19, No. 1 pp. 181–192, 1986.
"Opposite Actions of CCK–8 on Amphetamine–Induced Hyperlocomotion, etc.", F. Weiss, et al, *Pharmacology Biochemistry & Behavior*, vol. 30, pp. 3098,317 (1988).
"CCK–8 Modulation of Mesolimbic Dopamine: Antagonism of Amphetamine–Stimulated Behaviors", L.H.Schneider, et al, *Peptides*, vol. 4, pp. 749–753, 1983.
"Gastrointestinal Hormones and Gastric Secretion", S.J.Konturek, *Gastrointestinal Hormones*, Ch.23, pp. 529–564 (1980) ed. G.B.J. Glass, Raven Press, NY.
"Role of Gastrin and Gastrin Receptors on the Growth of a Transplantable Mouse Colon Carcinoma, etc.", *Cancer Research 44*, 1612–1616, Apr., 1986.
"Effects of Gastrin, Proglumide, and Somatostatin on Growth of Human Colon Cancer", *Gastroenterology* 1988; 95: 1541–8.
"The Physiology of Cholecystokinin in Brain and Gut", G.J. Dockray, *British Medical Bulletin* (1982) vol. 38, No. 3, pp. 253–258.
"The Neuroendocrine Control of Appetite, etc.", John E. Morley, *Life Sciences*, vol. 27, pp. 355–368 (1980).
"Immunochemical Evidence of Cholecystokinin Tetrapeptides in Hog Brain", Rehfeld and Gotterman, *Journal of Neurochemistry*, vol. 32, pp. 1339–1341.
"Cholecystokinin Octapeptide: Continuous Picomole Injections, etc.", Della–Fera and Baile, *Science*, vol.26, pp. 471–473 (1979).
"Heterogeneity of GABAergic Cells In Cat Visual Cortex", H.Demeulemeester, et al, *The Journal of Neuroscience*, Mar. 1988 (8(3):988–1000.
"Hypnotics and Sedatives", Stewart C. Harvey, *The Pharmacological Basis of Therapeutics*, 1985, pp. 339–371.
"Synthesis and some reactions of 3–phenyl(1H, 3H)–quinazoline–2–thione–4–one", El–Deen and El–Desuky, *J.Serb.Chem.Soc.57*(11)719–723 1992).

(List continued on next page.)

*Primary Examiner*—Matthew V. Grumbling
*Attorney, Agent, or Firm*—Elizabeth M. Anderson

[57] ABSTRACT

Novel quinazolinone derivatives with good binding affinity for the CCK-A and CCK-B receptors, pharmaceutical compositions containing them, methods of using them and a novel process for their preparation are taught. The compounds are useful agents to suppress appetite, reduce gastric acid secretion, and the like.

9 Claims, No Drawings

OTHER PUBLICATIONS

"Synthesis and Anticonvulsant Activity of Some New 2–Substituted 3–Aryl–4(3H)–quinazolinones", James F. Wolfe, et al *J.Med.Chem.* 1990, 33, pp. 161–166.

"Synthesis of the 1,2,4–Triazolo[4,3–a]quinazolin–5–ones and Related Compounds", H.A. El–Sherief, et al *Bull.Chem.Soc.Jpn.,* 56, 1227–1230 (1983).

"Synthesis and Pesticidal Activity of some Quinazolin–4(3H)–one Derivatives", Gupta & Pandey, *Pestic.Sci.* 26, 1989, 41–49.

"Synthesis of some novel quinazolone thiosemicarbazide and thiazoline derivatives for potential anti–microbial activity", Omar, et al, *Eur.J.Med.Chem.–Chemica Therapeutica,* Jan.–Feb., 1981–16, No. 1, pp. 77–80.

"Effect of Gastrointestinal Hormones on Growth of Gastrointestinal Tissue", L. R. Johnson, *Gastrointestinal Hormones*, pp. 507–527, 1980.

"Gastrinomas", Fl. Stadil, *Gastrointestinal Hormones*, pp. 729–739, 1980.

"Inhibition of Synaptic Transmission in the Hippocampus by Cholecystokinin (CCK) and its Antagonism by a CCK Analog (CCK$_{27-33}$)" Elsevier, B.A.MacVicar *Basic Research*, 406:3/130–135 (1987).

Innis R.B., Snyder S.H., *Proc.Natl. Acad. Sci. USA*, 77:6917–6921 (1980).

Moran, T.H., et al, *Brain Research*, 362: 175–179 (1989).

*Cholecystokinin: Isolation, Structure and Functions*, G.B.J. Glass, Ed., Raven Press, New York, 1980, pp. 169–221.

*Cholecystokinin in the Nervous System*, J. de Belleroche and G.J. Dockray, Ed., Ellis Horwood, Chichester, England (1984) pp. 110–127.

*Tips* 11:271–273 (1990).

Woodruff G.N. and Hughes J., *Ann.Rev. Pharmacol. and Toxicol.*, 31:469–501 (1991).

QUINAZOLINONE DERIVATIVES AS CHOLECYSTOKININ (CCK) LIGANDS

This is a divisional of application Ser. No. 08/500,436 filed on Jul. 10, 1995, now U.S. Pat. No. 5,756,502 which is a continuation-in-part of Ser. No. 08/287,454, filed Aug. 8, 1994 now abandoned.

TECHNICAL FIELD

The invention pertains to quinazoline materials. In particular, the invention is concerned with central cholecystokinin (CCK) antagonists and, in particular, the materials that have a binding affinity for the CCK-B receptor.

BACKGROUND ART

Cholecystokinin is structurally and functionally related to gastrin. The active C-terminal tetrapeptide amide of gastrin is duplicated in cholecystokinin. The major structural difference that dictates whether a peptide of the CCK-gastrin family has a gastrin-like or CCK-like pattern of activity is the position of the tyrosyl residue and whether or not it is sulfated. *Gastrointestinal Hormones*, edited by George B. Jerzy, Glass Raven Press, New York, 1980, pp. 512–513. CCK is a polypeptide which was originally isolated from the gut. Later investigations, however, discovered CCK is also localized in the mammalian central nervous system; particularly high levels of the octapeptide form (CCK-8) are found in hippocampus. Immunocytochemical staining has revealed that CCK-8 containing neurons appear to be interneurons in the hippocampus. "Inhibition of Synaptic Transmission in the Hippocampus by Cholecystokinin (CCK) and its Antagonism by a CCK Analog ($CCK_{27-33}$)" (Elsevier, B. A. MacVicar, J. P. Kerrin, and J. S. Davison, *Basic Research* 406:130–135, 1987).

Agents acting at central cholecystokinin (CCK) receptors may induce satiety (Schick, Yaksh, and Go, *Regulatory Peptides* 14:277–291, 1986). They are also expected to act as analgesics (Hill, Hughesm and Pittaway, *Neuropharmacology* 26:289–300, 1987), and as anticonvulsants (MacVicar, Kerrin, and Davison, *Brain Research* 406:130–135, 1987).

Reduced levels of CCK-peptides have been found in the brains of schizophrenic patients compared with controls (Roberts, et al., *Brain Research* 288:199–211, 1983). It has been proposed that changes in the activity of CCK neurones projecting to the nucleus accumbens may play a role in schizophrenic processes by influencing dopaminergic function (Totterdell and Smith, *Neuroscience* 19:181–192, 1986). This is consistent with numerous reports that CCK peptides modulate dopaminergic function in the basal ganglia and particularly the nucleus accumbens (Weiss, Tanzer, and Ettenberg, *Pharmacology, Biochemistry and Behaviour* 30:309–317, 1988; Schneider, Allpert, and Iversen, *Peptides* 4:749–753, 1983). It may therefore be expected that agents modifying CCK receptor activity may have therapeutic value in conditions associated with disturbed function of central dopaminergic function such as schizophrenia and Parkinson's disease.

CCK and gastrin peptides share a common carboxy terminal pentapeptide sequence, and CCK peptides can bind to the gastrin receptor of the stomach mucosa and elicit acid secretion in many species including human (Kontruek, *Gastrointestinal Hormones*, Ch. 23:529–564, 1980, ed. G. B. J. Glass, Raven Press, N.Y.). The receptors for CCK have been classified into two subtypes according to their affinity for CCK fragments and their analogs. CCK-A receptors are found predominantly in peripheral tissues such as pancreas and gall bladder. They have high affinity for the sulfated octapeptide (CCK-8S) and lower affinity for the corresponding desulfated fragment CCK-8d, CCK-4 and gastrin. Conversely, CCK-B receptors are widely distributed throughout the brain and exhibit high affinity for CCK-8s, CCK-4 and gastrin. (Innis, R. B.; Synder, S. H., *Proc. Natl. Acad. Sci. USA*, 77:6917–6921, 1980 and Moran, T. H., et al., *Brain Research*, 362:175–179, 1989). Antagonists of the CCK-B receptor would also be expected to be antagonists at the stomach gastrin receptor, and this would also be of value for conditions involving excessive acid secretion.

CCK and gastrin peptides have trophic effects on the pancreas and various tissues of the gastrointestinal tract (Johnson, *Gastrointestinal Hormones*, edited by George B. Jerzy Glass, "Effect of Gastrointestinal Hormones on Growth of Gastrointestinal Tissue," Chapter 22:507–527), actions which are associated with increased DNA and RNA synthesis. Moreover, gastrin secreting cells are associated with certain gastrointestinal tumors as in the Zollinger-Ellison syndrome (Stadil, *Gastrointestinal Hormones*, edited by George B. Jerzy Glass, "Gastrinomas," Chapter 30:729–739), and some colorectal tumors may also be gastrin/CCK dependent (Singh, et al., *Cancer Research* 46:1612, 1986; Smith, J. P., *Gastroenterology* 95:1541, 1988). Antagonists of CCK/gastrin receptors could therefore be of therapeutic value as antitumor agents.

The CCK peptides are widely distributed in various organs of the body including the gastrointestinal tract, endocrine glands, and the nerves of the peripheral and central nervous systems. Various biologically active forms have been identified including a 33-amino acid hormone and various carboxylterminus fragments of this peptide (e.g., the octapeptide $CCK_{26-33}$ and the tetrapeptide $CCK_{30-33}$). (G. J. Dockray, *Br. Med. Bull.* 38(3):253–258, 1982).

The various CCK peptides are thought to be involved in the control of smooth muscle contractility, exocrine and endocrine gland secretion, sensory nerve transmission, and numerous brain functions. Administration of the native peptides cause gall bladder contraction, amylase secretion, excitation of central neurons, inhibition of feeding, anticonvulsive actions and other behavioral effects. (*Cholecystokinin: Isolation, Structure and Functions*, G. B. J. Glass, ed., Raven Press, New York, 1980, pp. 169–221; J. E. Morley, *Life Sciences* 27:355–368, 1980; *Cholecystokinin in the Nervous System*, J. de Belleroche and G. J. Dockray, ed., Ellis Horwood, Chichester, England, 1984, pp. 110–127).

The high concentrations of CCK peptides in many brain areas also indicate major brain functions for these peptides (G. J. Dockray, *Br. Med. Bull.* 38(3):253–258, 1982). The most abundant form of brain CCK found is $CCK_{26-33}$, although small quantities of $CCK_{30-33}$ exist (Rehfeld and Gotterman, *J. Neurochem.* 32:1339–1341, 1979). The role of central nervous system CCK is not known with certainty, but it has been implicated in the control of feeding (Della-fera and Baile, *Science* 206:471–473, 1979).

Currently available appetite suppressant drugs either act peripherally, by increasing energy expenditure (such as thyroxine), or in some other manner (such as the biguanides), or act by exerting a central effect on appetite or satiety.

Centrally acting appetite suppressants either potentiate central catecholamine pathways and tend to be stimulants (for example, amphetamine), or influence serotonergic pathways (for example, fenfluramine). Other forms of drug therapy include bulking agents which act by filling the stomach, thereby inducing a "feeling" of satiety.

CCK is known to be present in some cortical interneurones which also contain gamma-aminobutyric acid (GABA) (H. Demeulemeester, et al., *J. Neuroscience* 8:988–1000, 1988). Agents that modify GABA action may have utility as anxiolytic or hypnotic agents ((S. C. Harvey, *The Pharmacological Basis of Therapeutics* (7th ed.) 1985, pp. 339–371, MacMillan)). Thus, agents which modify CCK action may have parallel anxiolytic or hypnotic activities. The role of CCK in anxiety is disclosed in *TIPS* 11:271–273, 1990, and is fully detailed in Woodruff, G.N. and Hughes, J., 1991, *Ann. Rev. Pharmacol. and Toxicol.* 31, 469–501.

Since the identification in brain extracts of the carboxyl (C)-terminal octapeptide of CCK-8, much evidence has arisen to suggest that CCK-related peptides have neuroregulatory roles in the central nervous system (CNS) in addition to their well-known hormonal functions in controlling digestion. The Physiology of Cholecystokinin in Brain and Gut, *British Medical Bulletin*, 38(3):353–358, 1982, by G. J. Dockray.

It is an object of the present invention to described pharmaceutical compositions that are effective to suppress the appetite in a mammal.

It is another object of the present invention to describe compositions that are effective to reduce gastric acid secretion in a mammal.

It is yet another object of the present invention to describe compositions useful to effect a reduction of anxiety in a mammal.

It is still another object of the present invention to describe compositions useful to effectively treat gastrointestinal ulcers in a mammal.

It is another object of the present invention to describe compositions useful to effectively treat psychotic behavior in a mammal.

Still further, it is an object of the present invention to describe compositions useful to effectively block the reaction caused by withdrawal from drug or alcohol use in a mammal.

It is still a further object of the present invention to describe compositions useful to effectively potentiate the affects of morphine and other opioids in treating pain in a mammal.

It is yet another object of the present invention to describe compositions useful to effectively treat and/or prevent panic in a mammal.

It is an object of the present invention to describe compositions which can be radio labeled and are useful for effecting diagnosis of gastrine-dependent tumors in a mammal.

It is a further object of the present invention to produce a key intermediate in the present invention by reacting the 2-hydrazine quinazoline derivative with hydrogen to obtain the 2-amino quinazoline derivative.

SUMMARY OF THE INVENTION

The invention relates to a method of treating a condition advantageously affected by the binding of a compound of Formula I to a CCK receptor in a mammal in need of such treatment comprising providing an effective binding amount of the compound of Formula I and a pharmaceutically acceptable salt thereof to such patient:

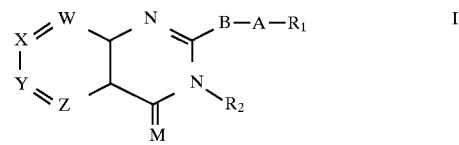

wherein W, X, Y and Z are each independently selected from C—$R_3$, C—$R_4$, C—$R_5$, C—$R_6$ and N (nitrogen) and that no more than two of W, W, Y and Z are N;

wherein $R_3$, $R_4$, $R_5$ and $R_6$ are each independently hydrogen, hydroxy, sulfhydryl, lower alkoxy (1–4 carbon atoms), lower thioalkoxy (1–4 carbon atoms), lower alkyl (1–4 carbon atoms), halo, CN, $CF_3$, $NO_2$, $COOR_7$ or $NR_7R_8$;

wherein $R_7$ and $R_8$ are independently hydrogen or lower alkyl (1–4 carbon atoms);

M is oxygen or sulfur;

B is defined as a direct bond or,

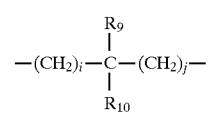

wherein i and j are independently 0 or 1;

$R_9$ and $R_{10}$ are independently hydrogen, lower alkyl (1–4 carbon atoms) or lower alkoxy (1–4 carbon atoms);

A is selected from the group consisting of:

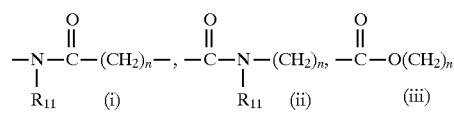

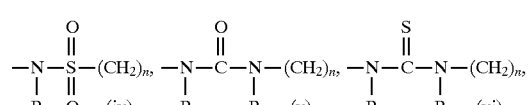

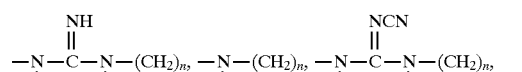

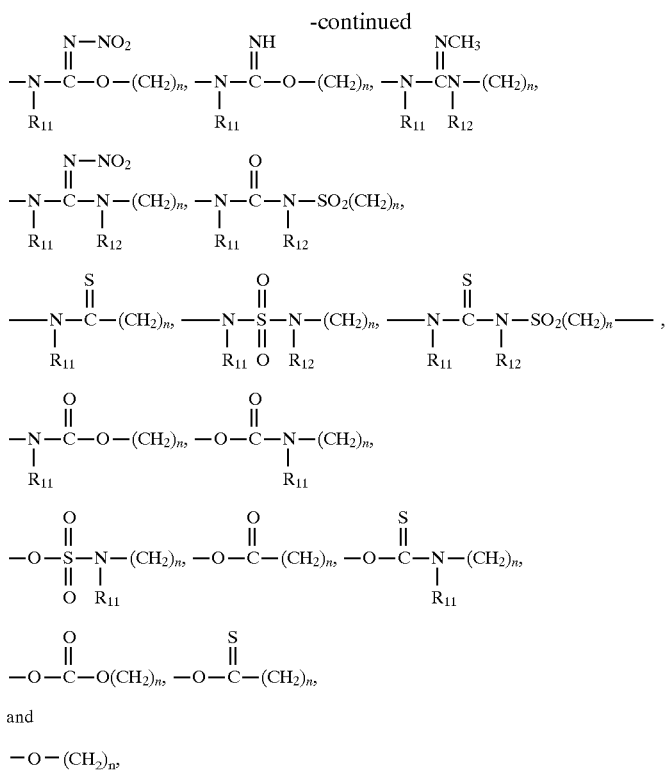

wherein $R_{11}$ and $R_{12}$ are independently hydrogen or lower alkyl (1–4 carbon atoms); n=0 or 1;

$R_1$ is:
an alkyl of 1 to 6 carbon atoms,
unsubstituted, mono- or polysubstituted phenyl or polyaromatic,
unsubstituted, mono- or polysubstituted heteroaromatic, with hetero atom(s) N (nitrogen), O (oxygen), and/or S (sulfur) or,
unsubstituted, mono- or polysubstituted aralkyl,
unsubstituted, mono- or polysubstituted cyclo or polycycloalkyl hydrocarbon, or
mono- or polyheterocycle (3 to 8 atoms per ring) with 1 to 4 hetero atoms as N (nitrogen), O (oxygen), or S (sulfur); and
wherein the substitutions are selected from hydrogen, methyl, methoxy, fluorine, bromine, chlorine, iodine, trifluoromethyl, cyano, acetyl, carboxy, carbmethoxy, carbethoxy, amino, N,N-dimethylamino, amido, acetyl, methylene carboxy, tetrazole, nitro, cyclohexyl, and adamantyl;

$R_2$ is:
an alkyl of 1 to 6 carbon atoms,
unsubstituted, mono- or polysubstituted phenyl or polyaromatic,
unsubstituted, mono- or polysubstituted heteroaromatic with heteroatom(s) N (nitrogen), O (oxygen), and/or S (sulfur) or,
unsubstituted, mono- or polysubstituted aralkyl,
unsubstituted, mono- or polysubstituted cyclo or polycycloalkyl hydrocarbon, or
mono- or polyheterocycle (3–8 atoms per ring) with 1 to 4 heteroatoms as N (nitrogen), O (oxygen), or S (sulfur);
wherein substitutions are selected from hydrogen, methyl, methoxy, fluorine, chlorine, bromine, iodine, hydroxy, ethoxy, propoxy, i-propoxy, t-butoxy, ethyl, propyl, i-propyl, trifluoromethyl, 3-cyclopropoxy, thioisopropyl, cyano, N,N-dimethylamino, N,N-dimethylamino methyl, carboxy, carbmethoxy, and tetrazole.

The invention is also concerned with utilizing the composition of Formula I in an effective amount to suppress the appetite in a mammal.

The invention is also concerned with using the compound of Formula I to reduce the gastric acid secretion in a mammal.

The invention is also concerned with the composition of Formula I to reduce anxiety in a mammal.

The invention is also concerned with using the composition of Formula I to treat gastro intestinal ulcers in a mammal.

The invention is also concerned with the composition of Formula I used to treat psychotic behavior in a mammal.

The invention is also concerned with utilizing the composition of Formula I to block the reaction caused by withdrawal from a drug or alcohol use in a mammal.

The invention is also concerned with utilizing the composition of Formula I to potentiate the effects of morphine and other opioids in treating pain.

The invention is also concerned with utilizing the composition of Formula I to treat and/or prevent panic in a mammal.

The invention is also concerned with utilizing the composition of Formula 1 as a diagnostic tool for gastrine dependent tumors in a mammal by utilizing a radio labeled iodo compound of Formula I.

The invention is also concerned with producing compound of Formula I by reacting an amine $R_2NH_2$ with a precursor aromatic acid of Formula II described below.

The invention is also concerned with the compounds of Formula I having the definition for the respective portions thereof as defined below in Formula III.

The invention is also concerned with a process for producing compounds of Formula IB.

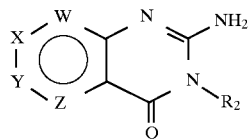

by hydrogenating the hydrazine derivative of Formula IC:

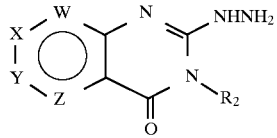

DESCRIPTION OF PREFERRED EMBODIMENTS

Preferred compounds of the instant invention are those of Formula I, wherein:

W and Y are each independently C—$R_3$, C—$R_5$ or N,
X and Z are each independently C—$R_4$ or C—$R_6$,
  wherein $R_3$, $R_4$, $R_5$ and $R_6$ are each independently chlorine, bromine, iodine, carbmethoxy, carboxy, methoxy, methyl, thio, thiomethyl, thioethyl, and hydroxy;
M is O or S;
B is a direct bond, or

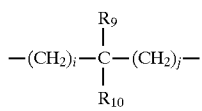

wherein i and j are independently 0 or 1, and $R_9$ and $R_{10}$ are independently hydrogen or methyl;

A is selected from

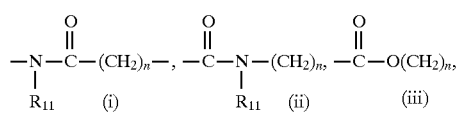

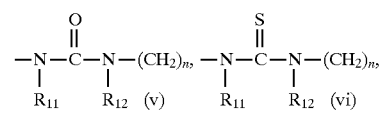

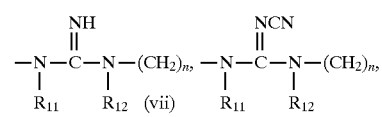

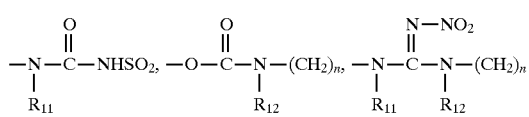

wherein $R_{10}$ and $R_{11}$ are independently hydrogen, n is 0 or 1;

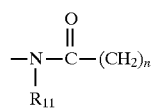

provided one or both of W and Y is N (nitrogen) when A is any of of i-viii, wherein $R_{11}$ is as defined above;

$R_1$ is an unsubstituted, mono- or polysubstituted
  phenyl,
  pyridyl,
  pyrrolyl,
  furanyl,
  thiofuranyl,
  pyrimidinyl,
  indolyl,
  quinolinyl,
  quinaxolinyl; or
  a cyclo or polycycloalkyl hydrocarbon of 6 to 12 carbon atoms;
wherein the substituents are indicated above, preferably up to three substituents;

$R_2$ is an unsubstituted, mono- or polysubstituted
  phenyl,
  pyridyl,
  pyrrolyl,
  furanyl,
  thiofuranyl,
  pyrimidinyl,
  indolyl,
  quinolinyl,
  quinoxolinyl; or
  a cyclo or polycycloalkyl hydrocarbon of 6 to 12 carbon atoms;
wherein the substituents are indicated above, preferably up to three substituents.

More preferred compounds of the instant invention are those of Formula I, wherein:

W is C—$R_3$ or N wherein $R_3$ is selected from hydrogen, chlorine, bromine, iodine, methoxy, and methyl;
X is C—$R_4$ wherein $R_4$ is selected from hydrogen, chlorine, hydroxy, methoxy, sulfhydryl and thioethylether;
Y is C—$R_5$ wherein $R_5$ is selected from hydrogen, chlorine, bromine, iodine, methoxy, methyl, carboxy, and carbmethoxy;
Z is C—R6 and N, wherein $R_6$ is hydrogen;
M is oxygen or sulfur;
B is a direct bond or,

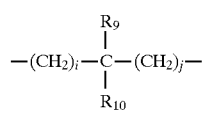

wherein i and j are independently 0 o r 1;

$R_9$ and $R_{11}$ are independently hydrogen or methyl; A is selected from

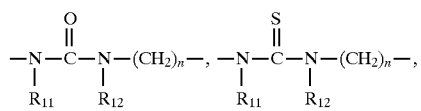

-continued

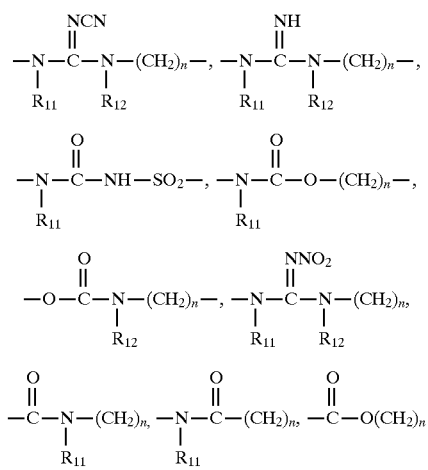

wherein $R_{11}$ and $R_{12}$ are independently hydrogen; n is 0 or 1;

provided one or both of W and Y is/are nitrogen wherein n and $R_{11}$ are as defined above;

$R_1$ is phenyl,
  mono- or polysubstituted phenyl,
  pyridyl,
  pyrrolyl,
  furanyl,
  thiofuranyl,
  pyrimidinyl,
  indolyl,
  quinolinyl,
  quinaxolinyl;
wherein substitutions are selected from hydrogen, methyl, methoxy, fluorine, bromine, chlorine, iodine, trifluoromethyl, cyano, acetyl, carboxy, carbmethoxy, carbethoxy, amino, N,N-dimethylamino, amido, acetyl, methylene carboxy, tetrazole, nitro, cyclohexyl, or adamantyl;

$R_2$ is phenyl,
  mono- or polysubstituted phenyl,
  pyridyl,
  pyrrolyl,
  furanyl,
  thiofuranyl,
  pyrimidinyl,
  indolyl,
  quinolinyl,
  quinoxolinyl;
wherein substitutions are selected from hydrogen, methyl, methoxy, fluorine, chlorine, bromine, iodine, hydroxy, ethoxy, propoxy, i-propoxy, t-butoxy, ethyl, propyl, i-propyl, trifluoromethyl, 3-cyclopropoxy, thioisopropyl, cyano, N,N-dimethylamino, N,N-dimethylamino methyl, carboxy, carbmethoxy, or tetrazole.

Scheme I illustrates preparative steps in the process of making key intermediates to prepare desired compounds of the instant invention. Coupling of 1 with an appropriate N-carbobenzyloxy amino acid 2 using a coupling agent such as 1,1'-carbonyldiimidazole (CDI) can give 3. Hydrolysis of 3, using a base such as lithium hydroxide can produce 4 which can be then coupled with an appropriate amine using a coupling agent such as 1,1'-carbonyldiimidazole to give quinazolinone derivative 5. Alternatively, 5 can be prepared stepwise by coupling with an appropriate amine followed by cyclization by treatment with p-toluene-sulfonic acid or pyridinium p-toluene-sulfonate. Deprotection of amino function of compound 5 by hydrogenolysis using palladium on charcoal can give the corresponding free amine 6 (Intermediate a). In Scheme I, the acid reagent 2 uses the abbreviation "CBz" which means —$COOCH_2C_6H_5$—.

Scheme II illustrates the process of making intermediates useful in preparation of desired compounds of the instant invention. (See British Patent No. 1,038,729 and U.S. Pat. No. 3,867,384). Treatment of 7 with an appropriate isothiocyanate in refluxing acetic acid can give the Compound 8. The chlorination of the compound 8 using sulfuryl chloride ($SO_2Cl_2$) can give Compound 9. Treatment of the chloro Compound 9 with ammonia can give the corresponding amino quinazolinone derivative 10 (Intermediate b). Alternatively, Compound 10 (Intermediate b) can be prepared by the method described in the literature (F. M. E. Abdel-Megeid, et al., *J. Chem. Soc.*, 1055–58 (1971)).

Scheme IIA illustrates the process of making intermediates useful in preparation of desired compounds of the instant invention. (Kottke, et al., *Pharmazie*, 37:635–637, (1982)). Treatment of 7 with an appropriate isothiocyanate in refluxing acetic acid can give Compound 8. Reaction of 8 with hydrazine in refluxing ethanol can give Compound 9A. Hydrogenolysis of 9A in presence of Raney Nickel can provide Compound 10.

The desired compounds of the instant invention can be prepared by acylation of intermediate a or intermediate b by an appropriate acylating agent as shown in Schemes III and IV.

Scheme IVa illustrates the process of making compounds of present invention by acylation of intermediate b by an appropriate acylating agent.

The compounds of the present invention can also be prepared as outlined in Scheme V. Coupling of 19 with an appropriate N-(tert-butoxycarbonyl) amino acid 20 using a coupling agent such as 1,1'-carbonyldiimidazole can give the corresponding amide 21 which can be deprotected by treating with hydrogen chloride to give the hydrochloride salt 22. Acylation of 22 in presence of a base such as triethylamine can give the urea derivative 23. Debenzylation of 23 can be achieved by hydrogenolysis using palladium on charcoal as a catalyst to give the free acid 24. Coupling of 24 with an appropriate amine with a coupling agent such as 1,1'-carbonyldiimidazole can directly give the corresponding desired product 25. Alternatively, the desired product can be obtained by coupling of 24 with an appropriate amine using a coupling agent such as 1,1'-carbonyldiimidazole and then treating it with p-toulenesulfonic acid or pyridinium p-toluene-sulfonate.

The compounds of the present invention can also be prepared by the method shown in Scheme VI. Coupling of 26 with an appropriate ω-benzylether acid 27 using a coupling agent such as 1,1'-carbonyldiimidazole can give the Compound 28 which can be hydrolyzed by a base such as lithium hydroxide to yield the corresponding acid 29. The quinazolinone derivative can be obtained directly by coupling with an appropriate amine by using a coupling agent such as 1,1'-carbonyldiimidazole or by coupling with an appropriate amine using a coupling agent such as 1,1'-carbonyldiimidazole and then cyclization by treating it with p-toluenesulfonic acid or pyridium p-toluenesulfonate. Free alcohol 31 can be obtained by hydrogenolysis of 30 using palladium on charcoal as a catalyst. Acylation of the free alcohol 31 with an appropriate isocyanate can give the desired product.

The compounds of the present invention can also be prepared by the method shown in Scheme VII. Coupling of 33 with ω-t-butylester acid 34 using coupling agent such as 1,1'-carbonyldiimidazole can give the Compound 35 which can be hydrolyzed by base such as LiOH to give the corresponding acid 36. The quinazolinone derivative 37 can be obtained directly by coupling with an appropriate amine by using a coupling agent such as 1,1'-carbonyldiimidazole or by coupling with an appropriate amine using a coupling agent such as 1,1'-carbonyldiimidazole and then cyclization by treating with p-toluenesulfonic acid or pyridium p-toluenesulfonate. Free acid 38 can be obtained by hydrolysis of t-butyl ester by acid such as HCl. Coupling of 38 with an appropriate amine or alcohol using a coupling agent such as 1,1'-carbonyldiimidazzole can give the corresponding amine 39 or ester 40, respectively.

The compounds can also be prepared by Scheme VIII which follows similar synthesis techniques of Scheme VII and also the synthesis techniques of U.S. Pat. No. 5,324,483 issued to Cody, et al., hereby incorporated by reference.

Compounds for which no preparation is given can be made by methods known in the literature or are of common knowledge by a skilled artisan.

The biological activity of compounds of the present invention may be evaluated by employing an initial screening test which rapidly and accurately measures the binding of the tested compound to known CCK receptor sites. Specific CCK receptors have been shown to exist in the central nervous system. (See Hays, et al., *Neuropeptides* 1:53–62, 1980; and Satuer, et al., *Science* 208:1155–1156, 1980).

In this screening test, the cerebral cortices taken from male CFLP mice weighing between 30 to 40 g were dissected on ice, weighed, and homogenized in 10 volumes of 50 mM Tris-HCl buffer (pH 7.4 at 0°–4° C.). The resulting suspension was centrifuged, the supernate was discarded, and the pellet was washed by resuspension in Tris-HCl buffer followed by recentrifugation. The final pellet was resuspended in 20 volumes of 10 nM Hepes buffer (pH 7.2 at 23° C.) containing 130 mM NaCl, 4.7 nM KCl, 5 nM $MgCl_2$, 1 nM (0.25 mg/mL).

In saturation studies, cerebral cortical membranes were incubated at 23° C. for 120 minutes in a final volume of 500 μL of Hepes incubation buffer (pH 7.2) together with 0.2–20 nM tritiated-pentagastrin (Amersham International, England).

In the displacement experiments, membranes were incubated with a single concentration (2 nM) of ligand, together with increasing concentrations ($10^{-11}$ to $10^{-14}$M) of competitive test compound. In each case, the nonspecific binding was defined as that persisting in the presence of the unlabeled octapeptide $CCK_{26-33}$ ($10^{-6}$M)

Following incubation, radioactivity bound to membranes was separated from that free in solution by rapid filtration through Whatman GF/B filters and washed three times with 4 mL of ice cold Tris-HCl buffer. Filters from samples incubated with tritiated-pentagastrin were placed in polyethylene vials with 4 mL of scintillation cocktail, and the radioactivity was estimated by liquid scintillation spectrometry (efficiency 47–52%).

The specific binding to CCK receptor sites was defined as the total bound tritiated-pentagastrin minus the amount of tritiated-pentagastrin bound in the presence of $10^{-6}$ octapeptide, $CCK_{26-33}$.

Saturation curves for specific tritiated-pentagastrin binding to mouse cortical membranes were analyzed by the methods of Scatchard (*Ann. New York Acad. Sci.* 51:660–672, 1949), and Hill (*J. Physiol.* 40:IV–VIII, 1910), to provide estimates for the maximum number of binding sites ($B_{max}$) and the equilibrium dissociation constant ($K_a$).

In displacement experiments, inhibition curves were analyzed by either logit-log plots or the iterative curve fitting computer program ALLFIT (DeLean, Munson, and Redbard, 1978) to provide estimates of the $IC_{50}$ and nH (apparent Hill coefficient values). ($IC_{50}$ values were defined as the concentration of test compound required to produce 50% inhibition of specific binding).

The inhibition constant ($K_i$) of the test compound was then calculated according to the Cheng-Prusoff equation:

$$K_i = \frac{IC_{50}}{1 + [L]/K_a}$$

where [L] is the concentration of radiolabel and $K_a$ is the equilibrium dissociation constant.

The $K_i$ values for several representative compounds of the present invention are present in Table 1.

TABLE 1

| n | X | R | CCK-A (Ki, nM) | CCK-B (Ki, nM) |
|---|---|---|---|---|
| 1 | O | $PhCH_2$ | 4480 | 620 |
| 1 | NH | 3-MePh | 1637 | 879 |
| 1 | NH | 3-COOEtPh | 1465 | 126 |
| 1 | NH | 4-BrPh | 984 | 137 |
| 1 | NH | $4-CF_3Ph$ | 674 | 691 |
| 1 | NH | $4-NO_2Ph$ | 385 | 212 |
| 1 | NH | $4-BrPhCH_2$ | 3100 | 652 |
| 1 | — | -2-Quinoxolinyl | 29% @ 10 μM | 842 |
| 1 | $NHSO_2$ | $4-CH_3Ph$ | >1 μM | >1 μM |
| 2 | O | $PhCH_2$ | 2770 | 768 |
| 2 | NH | 4-BrPh | 1630 | 585 |

The procedures described hereinbelow are useful for testing the utility of the compounds of the present invention as appetite suppressants.

In the Palatable Diet Feeding assay, adult male Hooded Lister rats weighing between 200–400 g are housed individually and trained to eat a palatable diet. This diet consists of Nestlés sweetened condensed milk, powered rat foot and rat water which, when blended together, set to a firm consistency. Each rat is presented with 20 to 30 g of the palatable diet for 30 minutes per day during the light phase of the light-dark cycle over a training period of 5 days. The intake of palatable diet is measured by weighing the food containing before and after the 30-minute access period (limits of accuracy 0.1 g). Care is taken to collect and correct for any spillage of the diet. Rats are given free access to pellet foot and water except during the 30-minute test period.

After the training period, dose-responsive curves are constructed for CCK8 and several representative compounds of the present invention (n=8–10 rats per dose level). $MPE_{50}$ values (±95% confidence limits) are obtained for the anorectic effects of these compounds.

In therapeutic use as appetite suppression agents, the compounds of the instant invention are administered to the patient at dosage levels of from about 200 to about 2800 mg per day.

Male Hooded Lister rats (175–250 g) are housed individually and are caused to fast overnight (free access to water). They are anesthetized with urethane (1.5 g/kg IP) and the trachea cannulated to aid spontaneous respiration. The stomach is perfused continuously using a modification of the original method of Ghosh & Schild in "Continuous Recording Of Acid Secretion In The Rat", *Brit. J. Pharmac.* 13:54–61, 1956 as described by Parsons in "Quantitative Studies of Drug-Induced Gastric Acid Secretion". (Ph.D.

Thesis, University of London, 1969). The cavity of the stomach is perfused at a rate of 3 mL/min with 5.4% w/v glucose solution through both the esophageal and body cannula. The fluid is propelled by a roller pump (Gilson, Minipuls 2), through heating coils to bring its temperature to 37°±1° C. The perfusion fluid is collected by the fundic collecting funnel and passed to a pH electrode connected to a Jenway pH meter (PHM6). An output is taken from the pH meter to a Rikadenki chart recorder for the on-line recording of the pH of the gastric perfusate.

Pentagastrin is stored as a frozen aliquot and diluted to the required concentrations with sterile 0.9% w/v NaCl. Novel compounds are dissolved in sterile 0.9% w/v NaCl on the day of the experiment. Drugs are administered IV through a cannulated jugular vein as a bolus in a dose volume of 1 mL/kg washed in with 0.15 mL 0.5% w/v NaCl. Basal pH is allowed to stabilize before administration of compounds is begun. Typically 30 minutes elapses between surgery and the first compound administration.

The compounds of the instant invention are also useful as antiulcer agents as discussed hereinbelow.

Aspirin-induced gastric damage is assessed in groups of 10 rats each.

All animals are made to fast for 24 hours before and during the experiment. Drug or vehicle is given 10 minutes before an oral dose of 1 mL of a 45-mg/ml suspension of aspirin in 0.5% carboxymethylcellulose (CMC).

The animals are sacrificed 5 hours after aspirin administration and the stomachs removed and opened for examination.

Gastric damage is scored as follows:

| Score | |
|---|---|
| 1 | Small hemorrhage |
| 2 | Large hemorrhage |
| 3 | Small ulcer |
| 4 | Large ulcer |
| 5 | Perforated ulcer |

The specific dosages may, however, be varied depending upon the patient, the severity of the condition being treated, and the activity of the compound employed. Determination of optimum dosages is within the skill of the art.

The compounds of the instant invention are also useful as anxiolytic agents as described and discussed below. Anxiolytic activity is assessed in the light/dark exploration test in the mouse (Jones, B. J., et al., *Brit. J. Pharmac.*, 93:985–993, 1988).

The apparatus used is an open-topped box, 45 cm long, 27 cm wide, and 27 cm high, divided into a small (2/5) area and a large (3/5) area by a partition that extended 20 cm above the walls. There is a 7.5×7.5 cm opening in the partition at floor level. The small compartment is painted black and the large compartment white. The floor of each compartment is marked into 9 cm squares. The white compartment is illuminated by a 100-watt tungsten bulb 17 cm above the box and the black compartment by a similarly placed 60 watt red bulb. The laboratory is illuminated with red light.

All tests are performed between 1300 hours, 0 minutes and 1800 hours, 0 minutes. Each mouse is tested by placing it in the center of the white area and allowing it to explore the novel environment for 5 minutes. Its behavior is recorded on videotape and the behavioral analysis is performed subsequently from the recording. Five parameters are measured: the latency to entry into the dark compartment, the time spent in each area, the number of transitions between compartments, the number of lines crossed in each compartment, and the number of rears in each compartment.

In this test, an increase in the time spent in the light area is a sensitive measure of, that is directly related to, the anxiolytic effects of several standard anxiolytic drugs. Drugs were dissolved in water or saline and administered either subcutaneously, intraperitoneally, or by mouth (PO) via a stomach needle.

The compounds of the instant invention are useful as antipsychotic agents and can be tested for their ability to reduce the effects of intra-accumbens amphetamine in the rat as described hereinafter.

Male Sprague Dawley (CD) Bradford strain rats are used. The rats are housed in groups of five at a temperature of 21°±2° C. on a 12 hour light-dark cycle of lights-on between 07 hours 00 minutes and 20 hours 00 minutes. Rats are fed CRM diet (Labsure) and allowed water ad libitum.

Rats are anesthetized with chloral hydrate (400 mg/kg SC) and placed in a Kopf stereotaxic frame. Chronically indwelling guide cannulae (constructed of stainless steel tubing 0.65 mm diameter held bilaterally in Parspex holders) are implanted using standard stereotaxic techniques to terminate 3.5 mm above the center of the nucleus accumbens (Ant. 9.4, Vert. 0.0, Lat. 1.6) or 5.0 mm above the central nucleus of the amygdala (Ant. 5.8, Vert. −1.8, Lat. ±4.5) (atlas of De Groot, 1959). The guides are kept patent during a 14-day recovery period using stainless steel stylets, 0.3 mm diameter, which extended 0.5 mm beyond the guide tips.

Rats are manually restrained and the stylets removed. Intracerebral injection cannulae, 0.3 mm diameter, are inserted and drugs delivered in a volume of 0.5 $\mu$L over 5 seconds (a further 55 seconds was allowed for deposition) from Hamilton syringes attached via polythene tubing to the injection units. Animals are used on a single occasion only.

Behavioral experiments are conducted between 07 hours 30 minutes and 21 hours 30 minutes in a quiet room maintained at 22°±2° C. Rats are taken from the holding room and allowed 1 hour to adapt to the new environment. Locomotor activity i9 assessed in individual screened Perspex cages (25×15×15 cm (high) (banked in groups of 30) each fitted with one photocell unit along the longer axis 3.5 cm from the side; this position has been found to minimize spurious activity counts due to, for example, preening and head movements when the animal is stationary. Interruptions of the light beam are recorded every 5 minutes. At this time animals are also observed for the presence of any nonspecific change in locomotor activity, e.g., sedation, prostration, stereotyped movements, that could interfere with the recording of locomotor activity.

The abilities of the compounds of the invention to inhibit the hyperactivity are tested as described hereinbelow.

An increase in locomotor activity followed the bilateral injection of amphetamine (20 $\mu$g) into the nucleus accumbens; peak hyperactivity (50 to 60 counts 5 minutes-$^{-1}$) occurs 20 to 40 minutes after injection. This test is known to be predictive of antipsychotic activity (Costall, et al., *Brit. J. Pharmac.*, 92:881–894).

The compounds of the instant invention prevent and treat the withdrawal response produced when chronic treatment by a drug is stopped or when alcohol abuse is stopped. These compounds are therefore expected to be useful as therapeutic agents in the treatment of chronic drug or alcohol abuse as discussed and described below.

The effect of the compounds of the instant invention is illustrated, for example, in the mouse "light/dark box" test wherein five animals are given nicotine, in a range of 0.1 to 100 mg/kg i.p. b.d. for 14 days. After a 24-hour withdrawal period, a compound of the invention is given at 1.0 mg/kg i.p. b.d. The increased time spent in the light area is a sensitive measure of the effect of a compound of the invention described herein as an agent to treat withdrawal effects from nicotine.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

The powders and tablets preferably contain 5% to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Pharmaceutically acceptable salts are acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydrochloride, hydroxynaphthoate, iodide, isethionate, lactate, lactobionate, malate, maleate, mandelate megylate, methylbromide, methylnitrate, methylsulfate, mucate, napsylate, nitrate, pamoate (embonate), pantothenate, phosphate/diphosphate, polygalacturonate, salicylate, stearate, subacetate, guccinate, sulfate, tannata, tartrate, teoclate, triethiodide, benzathine, chloroprocaine, choline, diethanolamine, ethylenediamine, meglumine, procaine, aluminum, calcium, lithium, magnegium, potassium, sodium, and zinc.

The term "preparation" is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form preparations include solutions, suspensions, and emulsions. Sterile water or water-propylene glycol solutions of the active compounds may be mentioned ag an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

EXAMPLE A

Benzoic acid, 2-[[[[(phenylmethoxy)carbonyl] amino]acetyl]amino]methyl ester

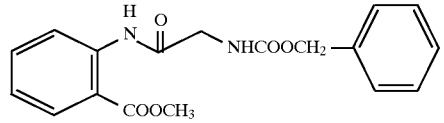

To a solution of carbobenzyloxy glycine (9.8 g, 47 mmol) in THF (100 mL) at room temperature was added 1,1-carbonyldiimidazole (8.1 g, 50 mmol). The reaction mixture was stirred under nitrogen for 1 hour, after which methyl anthranilate (6.3 g, 40 mmol) was added, and the reaction mixture was stirred for 24 hours at room temperature. The solvent was removed in vacuo. The resulting residue was dissolved in ethyl acetate (100 mL) and washed with water, 10% HCl, saturated NaHCO3, and brine. It was dried over $MgSO_4$ concentrated and crystallized from ethyl acetate to yield 7.6 g (55%) of the titled compound as a white solid, mp 121°–122° C.

EXAMPLE B

Benzoic acid, 2-[[[[(phenylmethoxy)carbonyl] amino]acetyl]amino]-

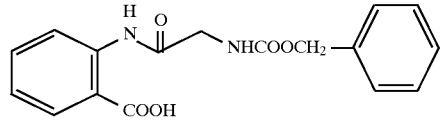

To a solution of benzoic acid, 2-[[[[(phenyl-methoxy) carbonyl]amino]acetyl]amino]-methyl ester (7.6 g, 22 mmol) in dioxane (100 mL) was added a solution of lithium hydroxide (1.4 g, 33 mmol) in water (20 mL). The reaction mixture was stirred for 24 hours and concentrated. The aqueous reaction mixture was acidified with 10% HCL. The solid separated was filtered and washed with water. Drying in vacuo at 60° C. provided the titled compound 7.0 g (95%) as a white solid, mp 155–156.

EXAMPLE C

Benzeneacetamide, N-[[3,4-dihydro-3[3-methylethoxyphenyl]-4oxo-2-quinazolinyl]methyl]-

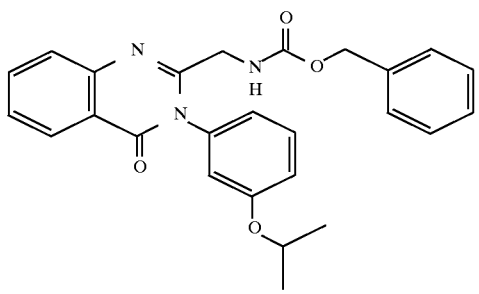

To a solution of 2-[[[[(phenylmethoxy)carbonyl]-amino]acetyl]amino]benzoic acid (3.35 g, 10 mmol) in 100 mL THF at room temperature was added 1,1-carbonyl-diimidazole (1.8 g, 11 mmol), and the reaction mixture stirred for an hour. To this reaction mixture, solution of 3-isopropoxy aniline (1.51 g, 10 mmol) in 25 mL THF was added and the mixture was heated to reflux overnight. The reaction mixture was cooled and solvent was removed in vacuo. The resulting residue was taken in ethyl acetate and washed with water, 1N HCl, saturated NaHCO$_3$, and brine. After drying over MgSO$_4$ and concentrating, it was chromatographed over silica gel (1:1 v/v ethyl acetate-hexane) provided 3.0 g (65%) of the titled compound as a white solid, mp 155° C.

EXAMPLE D

4(3H)-Quinazolinone, 2-(aminomethyl)-3-[3-methylethoxy)phenyl)-

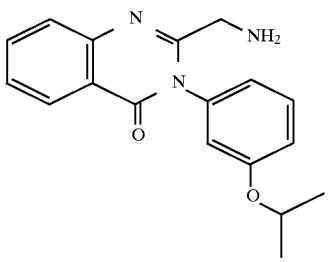

A solution of N-[[3,4-dihydro-3[3-methylethoxyphenyl]-4-oxo-2-quinazolinyl]methyl]-benzeneacetamide (1.47 g, 3.3 mmol) in 100 mL methanol was treated with 20% palladium on carbon (100 mg), and resulting suspension was subjected to an atmosphere of hydrogen at 51.9 psi for 4 hours with agitation at temperature of 30° C. This mixture was then filtered through celite, and the solvent was removed in vacuo to give 1.0 g (98%) of the titled compound as a yellow oil.

EXAMPLE E

Benzoic acid, 2-[[1-oxo-3-[[(phenylmethoxy)carbonyl]amino]propyl]amino]-methyl ester

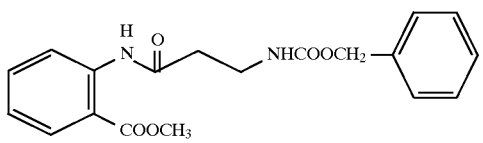

The title compound was prepared by the method as described for Example A, but using N-α-carbobenzyloxy-β-alanine instead of carbobenzyloxy glycine. The titled compound was obtained as a white solid in 58% yield, mp 75°–76° C.

EXAMPLE F

Benzoic Acid, 2-[[1-oxo-3-[[(phenylmethoxy)carbonyl]amino]propyl]amino]-

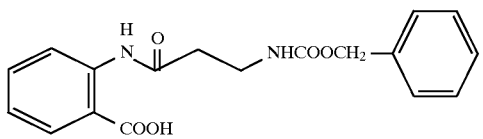

The title compound was prepared by the method as described for Example B, but using 2-[[1-oxo-3-[[(phenylmethoxy)carbonyl]amino]propyl]amino]-benzoic acid methyl ester. The title compound was obtained as a white solid in 90% yield, mp 150°–151° C.

EXAMPLE G

Carbamic acid, [2-[3,4-dihydro-3[3-(1-methylethoxy)phenyl)-4-oxo-2-quinazolinyl]ethyl-phenylmethyl ester

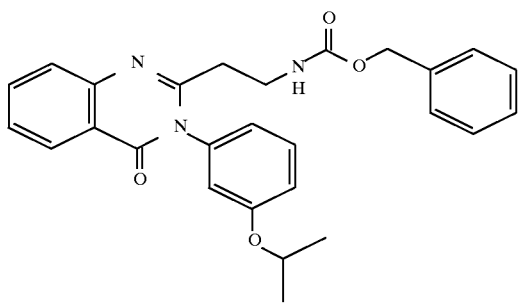

The title compound was prepared by the method as described for Example C, but using, 2-[[1-oxo-3-[[(phenylmethoxy)carbonyl]amino]propyl]amino]-benzoic acid. The titled compound was obtained as a white solid, mp 57°–58° C.

EXAMPLE H

4(3H)-Quinazoline, 2-(aminoethyl)-3-[3-methylethoxy)phenyl]-

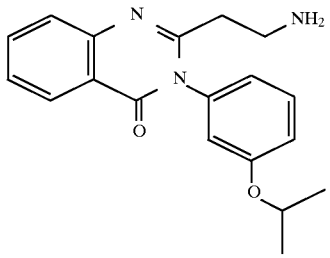

The title compound was prepared by the method as described for Example D, but using, [2-[3,4-dihydro-3-[3-(1-methylethoxy)phenyl]-4-oxo-2-quinazolinyl]ethyl-, phenylmethyl ester carbamic acid. The titled compound was obtained as a yellow oil.

EXAMPLE I 3-(3-Isopropoxy-phenyl)-2-thioxo-2,3-dihydro-1H-quinazolin-4-one

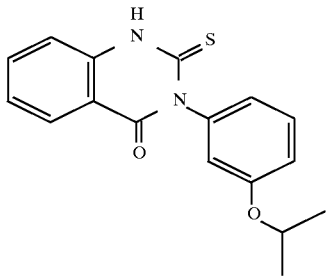

To a solution of 3-isopropoxy aniline (6.0 g, 40 mmol), in 150 mL of $CHCl_3$ was added dropwise thiophosgene (2.81 mL, 44 mmol) at 0° C. After the addition of thiophosgene, triethylamine (7.0 mL, 48 mmol) was added slowly and the reaction mixture was stirred for 2 hours at room temperature. It was then concentrated and diluted with 200 mL of ethyl acetate. The triethylamine hydrochloride salt was filtered off and the filtrate was concentrated to yield crude 3-isopropoxyphenyl isothiocyanate. The crude 3-isopropoxyphenyl isothiocyanate was dissolved in 150 mL of acetic acid, and anthranilic acid (6.04 g, 44 mmol) was added. The resulting reaction mixture was refluxed for 16 hours and then cooled to room temperature. The white solid was separated which was filtered to yield 9.0 g of the title compound (72.1%), mp 288°–290° C.

EXAMPLE J

2-Hydrazino-3-(3-isopropoxy-phenyl)-3H-quinazolin-4-one

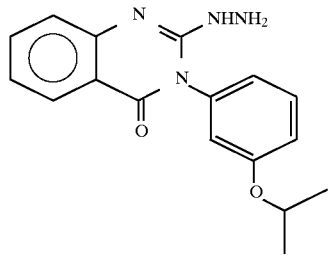

A mixture of 3-(3-isopropoxy-phenyl)-2-thioxo-2,3-dihydro-1H-quinazolin-4-one (Example 1) (3.12 g, 10 mmol) and anhydrous hydrazine (3.2 g, 100 mmol) in 100 mL of ethanol was refluxed for 18 hours. The reaction mixture was then cooled and white solid was separated which was filtered to obtain 1.2 g (38%) of title compound as white solid. The filtrate was concentrated and an additional 1.6 g (50.4%) of title compound was isolated by crystallization from ethyl acetate, mp 158°–160° C.

EXAMPLE K

2-Amino-3-(3-isopropoxy-phenyl)-3H-quinazolin-4-one

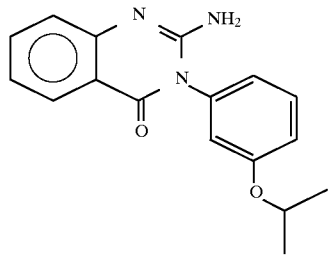

A solution of 2-Hydrazino-3-(3-isopropoxy-phenyl)-3H-quinazolin-4-one (2.5g, 8.0 mmol) in 100 mL methanol-THF (1:1) was treated with Raney Ni (2.0), and resulting suspension was subjected to atmosphere of hydrogen at 52.0 psi for 30 hours with agitation at temperature of 50° C. An additional 1.0 g of Raney Ni was added and reaction was continued for additional 40 hours at 50° C. The mixture was then filtered through celite, and the solvent was removed in vacuo to give the title compound as a reddish yellow solid. This crude product was then titurated with ethyl acetate and hexane to isolate 1.85 g (78%) product as a light yellow solid, mp 130°–133° C.

EXAMPLE 1

Urea, N-[[3,4-dihydro-3-[3-(1-methylethoxy)phenyl]-4-2-guinazolinyl]methyl]-N-(3-methylphenyl)

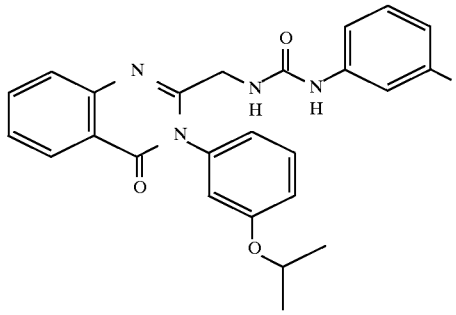

To a solution of 2-(aminomethyl)-3-[3-methylethoxy)phenyl)-4(3H)-Quinazoline (0.1 g, 0.33 mmol) in 15 mL ethyl acetate was added at room temperature 3-methylphenyl isocyanate (0.047 g, 0.35 mmol). The mixture was stirred for 2 hours. The solvent was removed in vacuo. The resulting product was chromatographed to give 70 mg (50%) of the titled compound as a white solid, mp 82°–87° C.

Analysis calculated for $C_{26}H_{26}N_4O_3:0.28C_4H_8O_2$: C, 69.72; H, 6.09; N, 11.99. Found: C, 69.64; H, 6.04; N, 12.12.

EXAMPLE 2

Urea, N-(4-bromophenyl)-N-[[3,4-dihydro-3-[3-(1-methylethoxy)phenyl]-4-2-quinazolinyl]methyl]-

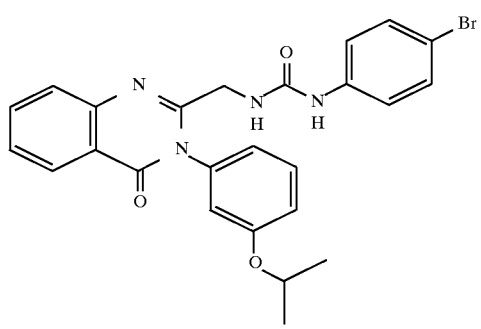

The title compound was prepared by the method as described for Example 1, but using 4-bromophenyl isocyanate. The titled compound was isolated as a white solid (80 mg, 50%), mp 125°–130° C.

Analysis calculated for $C_{25}H_{23}N_4O_3Br_1:0.1C_4H_8O_2$: C, 59.10; H, 4.65; N, 10.85; Br, 15.48. Found: C, 58.80; H, 4.68; N, 10.54; Br, 15.76.

EXAMPLE 3

Benzoic Acid, 3-[[[3,4-dihydro-3-[3-(1-methylethoxy)phenyl]-4-oxo-2-quinazolinyl]methyl]amino]carbonylamino-, ethyl ester

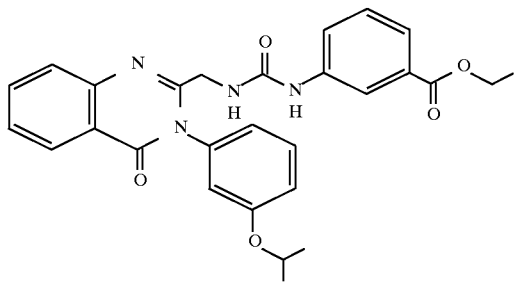

The title compound was prepared by the method as described for Example 1, but using 3-ethoxycarbonylphenyl isocyanate. The titled compound was isolated as a white solid (100 mg, 60%), mp 107°–109° C. Analysis calculated for $C_{28}H_{28}N_4O_5:0.3H_2O$: C, 66.47; H, 5.70; N, 11.07. Found: C, 66.51; H, 5.83; N, 10.84.

EXAMPLE 4

Urea, N-[[3,4-dihydro-3-[3-(1-methylethoxy)phenyl]-4-2-quinazolinyl]methyl]-N-[(4-trifluoromethyl)phenyl)]-

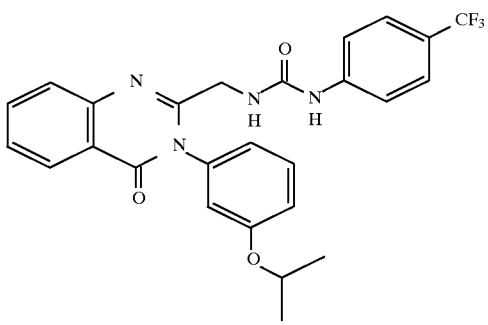

The title compound was prepared by the method as described in Example 1, but using 4-trifluoromethylphenyl isocyanate. The titled compound was isolated as a white solid (85 mg, 50%), mp 118°–122° C.

Analysis calculated for $C_{26}H_{23}N_4O_3F_3$: C, 62.90; H, 4.67; N, 11.28. Found: C, 63.26; H, 5.10; N, 11.32.

EXAMPLE 5

Benzenesulfonamide, N-[[[[3,4-dihydro-[3-(1-methylethoxy)phenyl]-4-oxo-2-guinazolinyl]methyl]amino]carboxy]-4-methyl

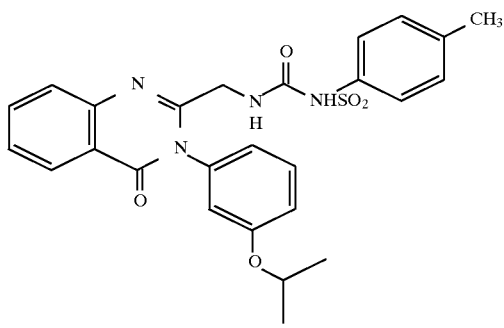

The title compound was prepared by the method as described for Example 1, but using 4-trifluoromethylphenyl isocyanate. The titled compound isolated as a white solid, mp 195°–206° C.

EXAMPLE 6

Urea, N-(4-bromophenyl)-N'-[2-[3,4-dihydro-3-[3-(1-methylethoxy)phenyl]-4-oxo-2-quinazolinyl]ethyl]-

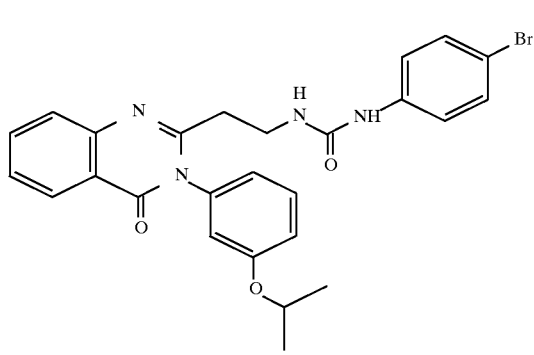

The title compound was prepared by the method as described for Example 2, but using 4(3H)-Quinazolinone, 2-(aminoethyl)-3-[3-methylethoxy)phenyl]. The titled compound isolated as a white solid (70 mg, 53%), mp 191°–192° C.

EXAMPLE 7

2-Quinoxalinecarboxamide, N-[[1,2-dihydro-3-[3-(1-methylethoxy)phenyl]-4-oxo-2-quinazolinyl]methyl]-

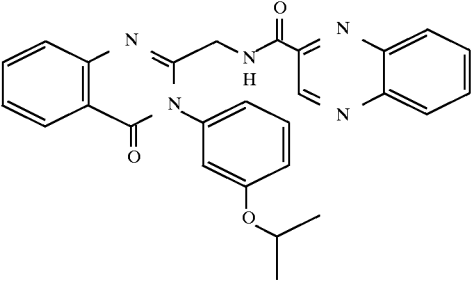

To a mixture of 2-(aminomethyl)-3-[3-methylethoxy)phenyl)-4(3H)-Quinazolinone (0.1 g, 0.33 mmol) and triethylamine (41 mg, 0.4 mmol) in 15 mL ethyl acetate was added 2-quinoxaloyl chloride (70 mg, 0.36 mmol) at room temperature. The reaction mixture was stirred overnight and then concentrated. It was then passed through silica gel and purified by HPLC (solvent system 1:1 Ethyl acetate:Hexane). The titled compound was obtained as a solid, (120 mg, 78%), mp 234°–236° C.

EXAMPLE 8

Carbamic acid, [[3,4-dihydro-3-[3-(1-methylethoxy)phenyl]-4-oxo-3-quinazolinyl]methyl]-, tricyclo [3.3.1.1$^{3.7}$]dec-1-yl ester

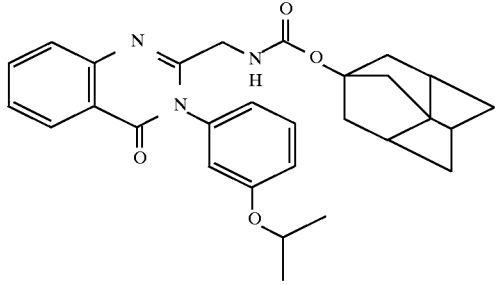

The title compound was prepared by the method as described for Example 7, but using 1-adamantyl fluoroformate, and it was purified by flash column chromatography. The title compound was isolated as a white solid (25 mg, 40.7%), mp 179°–180° C.

Analysis calculated for $C_{29}H_{33}N_3O_4$: C, 71.44; H, 6.82; N, 8.62. Found: C, 71.36; H, 6.83; N, 8.61.

EXAMPLE 9

1-(4-Bromo-phenyl)-3-[3-(3-isopropoxy-phenyl)-4-oxo-3,4-dihydro-quinazolin-2-ylmethyl]-thiourea

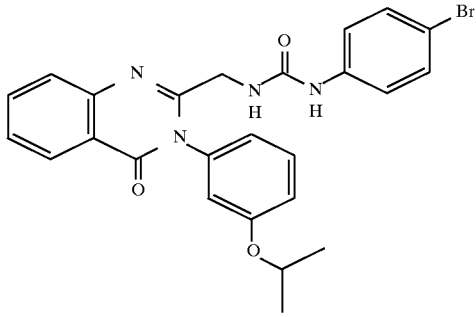

The title compound was prepared by the method was as described for Example 1, but using 4-bromophenyl isothiocyanate. The title compound was isolated as a gray solid (310 mg, 59.2%), mp 223°–24° C.

Analysis calculated for $C_{25}H_{23}N_4O_2S_1Br_1$: C, 57.36; H, 4.43; N, 10.70. Found: C, 57.12; H, 4.47; N. 10.46.

EXAMPLE 10

1-(4-Bromo-phenyl)-3-[3-(3-isopropoxy-phenyl)-4-oxo-3,4-dihydro-quinazolin-2-yl]-urea

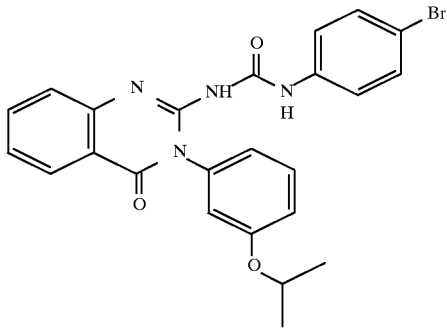

To a solution of 2-amino-3-(3-isopropoxy-phenyl)-3H-quinazolin-4-one (295 mg, 1.0 mmol) in anhydrous DMF (10 mL) was added 50% NaH (48 mg, 1 mmol) at room temperature and stirred for 30 minutes. To this mixture was added, 4-bromo phenyl isocyanate and stirred for 2 hours at room temperature. The reaction mixture was quenched with water and concentrated. It was then diluted with ethyl acetate and filtered. The filtrate was concentrated and chromatographed using 100% $CH_3Cl$ to isolate pure product as a white solid (70 mg, 14.2%), mp 230°–233° C.

Analysis calculated for $C_{24}H_{21}Br_1N_4O_3 \cdot 0.92 H_2O_1$: C, 56.53; H, 4.18; N. 10.95. Found: C, 56.53; H, 4.18; N, 10.98.

EXAMPLE 11

3-{3-[3-(3-Isopropoxy-phenyl)-4-oxo-3,4-dihydroquinazolin-2-yl]-ureido}-benzoic acid ethyl ester

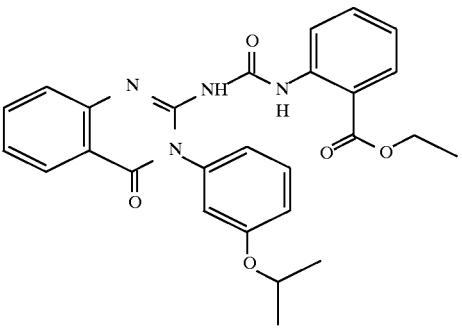

The title compound was prepared by the method as described for Example 10, but using 3-ethoxycarbonylphenyl isoccyanate. The title compound was isolated as a white solid (170 mg, 35%), mp 73°–76° C.

Analysis calculated for $C_{27}H_{22}N_4O_5$:

EXAMPLE 12

3-{3-[3-(3-Isopropoxy-phenyl)-4-oxo-3,4-dihydroquinazolin-2-yl]-ureido}-benzoic acid

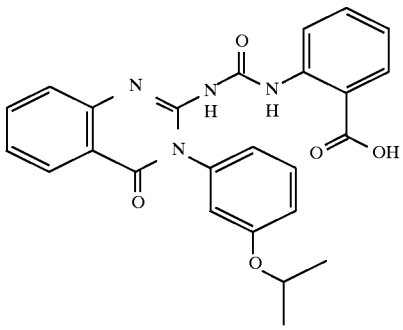

To a solution of 3-{3-[3-(3-Isopropoxy-phenyl)-4-oxo-3,4-dihydro-quinazolin-2-yl]-ureido}-benzoic acid ethyl ester (200 mg, 0.41 mmol) in 1,4-dioxane (10 mL) was added 1N LiOH (3 mL) and stirred overnight. The reaction mixture was acidified with 1N HCl and concentrated. It was then diluted with ethyl acetate and washed with water. The organic layer was dried over $MgSO_{41}$ concentrated and chromatographed using ethyl acetate:hexane (1:1 v/v) to isolate pure product as a white solid (150 mg, 80.2%), mp 158°–160° C.

Analysis calculated for $C_{25}H_{22}N_4O_5$: C, 65.49; H, 4.84; N, 12.22. Found: C, 65.49; H, 4.84; N, 12.03.

BIOLOGICAL TESTING

The following table represents the CCK-A and CCK-B receptor binding affinities of the compounds.

TABLE 1

[Structure: benzamide with N=C(CH₂)ₙ-NH-C(=O)-X-R substituent, N-phenyl with 3-isopropoxy group]

| n | X | R | CCK-A (Ki, nM) | CCK-B (Ki, nM) |
|---|---|---|---|---|
| 1 | O | PhCH₂ | 4480 | 620 |
| 1 | NH | 3-MePh | 1637 | 879 |
| 1 | NH | 3-COOEtPh | 1465 | 126 |
| 1 | NH | 4-BrPh | 984 | 137 |
| 1 | NH | 4-CF₃Ph | 674 | 691 |
| 1 | NH | 4-NO₂Ph | 385 | 212 |
| 1 | NH | 4-BrPhCH₂ | 3100 | 652 |
| 1 | — | -2-Quinoxolinyl | 29% @ 10 µM | 842 |
| 1 | NHSO₂ | 4-CH₃Ph | >1 µM | >1 µM |
| 2 | O | PhCH₂ | 2770 | 768 |
| 2 | NH | 4-BrPh | 1630 | 585 |

The testing procedures are disclosed in Hays, et al., *Neuropeptides* 1:53–62, 1980; and Satuer, et al., *Science* 208:1155–1156, 1980.

The compounds described herein are capable of further forming both pharmaceutically acceptable acid addition and/or base salts. All of these forms are within the scope of the present invention.

Pharmaceutically acceptable acid addition salts of the active compounds include salts derived from inorganic acids such as hydrochloric, nitric, phosphoric, sulfuric, hydrobromic, hydriodic, hydrofluoric, phosphorous, and the like, as well as the salts derived from organic acids, such as aliphatic mono- and dicarboxylic acids, phenyl-substituted alkanoic acids, hydroxy alkanoic acids, alkanedioic acids, aromatic acids, aliphatic and aromatic sulfonic acids, etc. Such salts thus include sulfate, pyrosulfate, bisulfate, sulfite, bisulfite, nitrate, phosphate, monohydrogenphosphate, dihydrogenphosphate, metaphosphate, pyrophosphate, chloride, bromide, iodide, acetate, trifluoroacetate, propionate, caprylate, isobutyrate, oxalate, malonate, succinate, suberate, sebacate, fumarate, maleate, mandelate, benzoate, chlorobenzoate, methylbenzoate, dinitrobenzoate, phthalate, benzenesulfonate, toluenesulfonate, phenylacetate, citrate, lactate, maleate, tartrate, methanesulfonate, and the like. Also contemplated are salts of amino acids such as arginate and the like and gluconate, galacturonate (see, for example, Berge S. M., et al., "Pharmaceutical Salts", *Journal of Pharmaceutical Science*, 66:1–19 (1977)).

The acid addition salts of said basic compounds are prepared by contacting the free base form with a sufficient amount of the desired acid to produce the salt in the conventional manner. Preferably, an active compound can be converted to an acidic salt by treating with an aqueous solution of the desired acid, such that the resulting pH is less than 4. The solution can be passed through a C18 cartridge to absorb the compound, washed with copious amounts of water, the compound eluted with a polar organic solvent such as, for example, methanol, acetonitrile, and the like, and isolated by concentrating under reduced pressure followed by lyophilization. The free base form may be regenerated by contacting the salt form with a base and isolating the free base in the conventional manner. The free base forms differ from their respective salt forms somewhat in certain physical properties such as solubility in polar solvents, but otherwise the salts are equivalent to their respective free base for purposes of the present invention.

Pharmaceutically acceptable base addition salts are formed with metals or amines, such as alkali and alkaline earth metals or organic amines. Examples of metals used as cations are sodium potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge S.M., et al., "Pharmaceutical Salts", *Journal of Pharmaceutical Science*, 66:1–19 (1977)).

The base addition salts of said acidic compounds are prepared by contacting the free acid form with a sufficient amount of the desired base to produce the salt in the conventional manner. Preferably, an active compound can be converted to a base salt by treating with an aqueous solution of the desired base, such that the resulting pH is greater than 9. The solution can be passed through a C18 cartridge to absorb the compound, washed with copious amounts of water, the compound eluted with a polar organic solvent such as, for example, methanol, acetonitrile and the like, and isolated by concentrating under reduced pressure followed by lyophilization. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention.

Certain of the compounds of the present invention can exist in unsolvated forms as well as solvated forms, including hydrated forms. In general, the solvated forms, including hydrated forms, are equivalent to unsolvated forms and are intended to be encompassed within the scope of the present invention.

Certain of the compounds of the present invention possess one or more chiral centers and each center may exist in the R(D) or S(L) configuration. The present invention includes all enantiomeric and epimeric forms as well as the appropriate mixtures thereof.

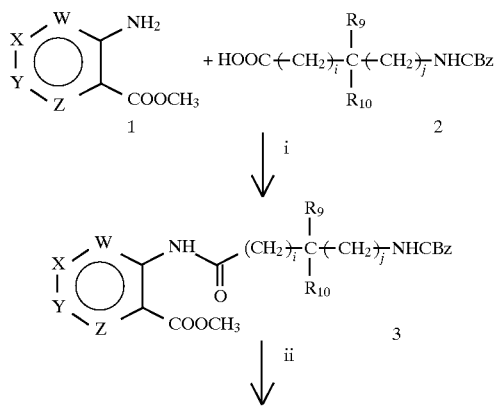

Scheme I

Scheme I -continued
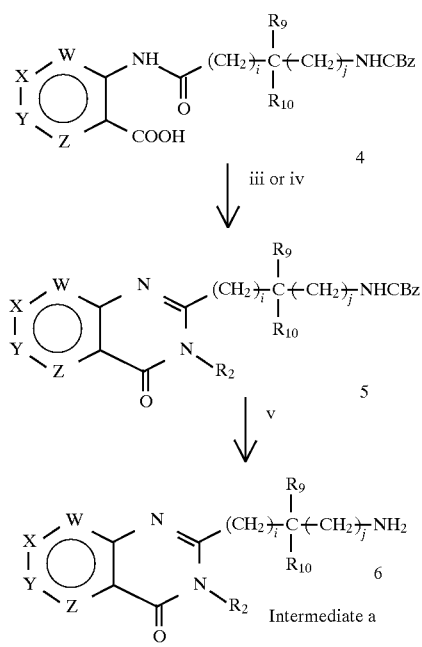
Key:
i) CDI, THF, reflux
ii) LiOH, Dioxane-water
iii) $R_2-NH_2$, CDI, reflux
iv) $R_2-NH_2$, CDI, and then PPTs
v) 10% Pd/C, $H_2$
Scheme II
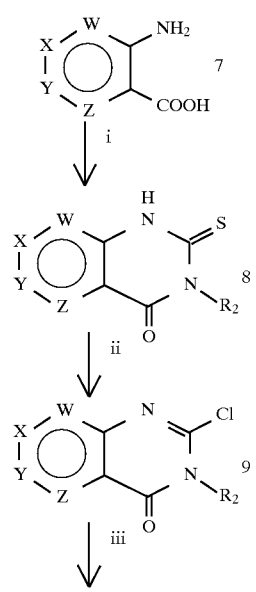
Scheme II -continued
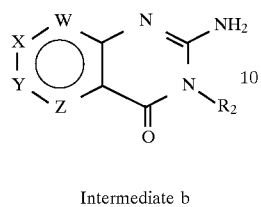
Intermediate b
Keys:
i) $R_2NCS$
ii) $SO_2Cl_2$
iii) $NH_3$
SCHEME IIA
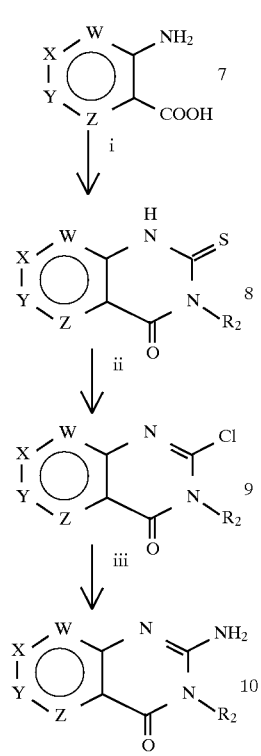
Intermediate b
Keys:
i) $R_2NCS$
ii) $NH_2NH_2$
iii) Raney Ni, $H_2$

Scheme III
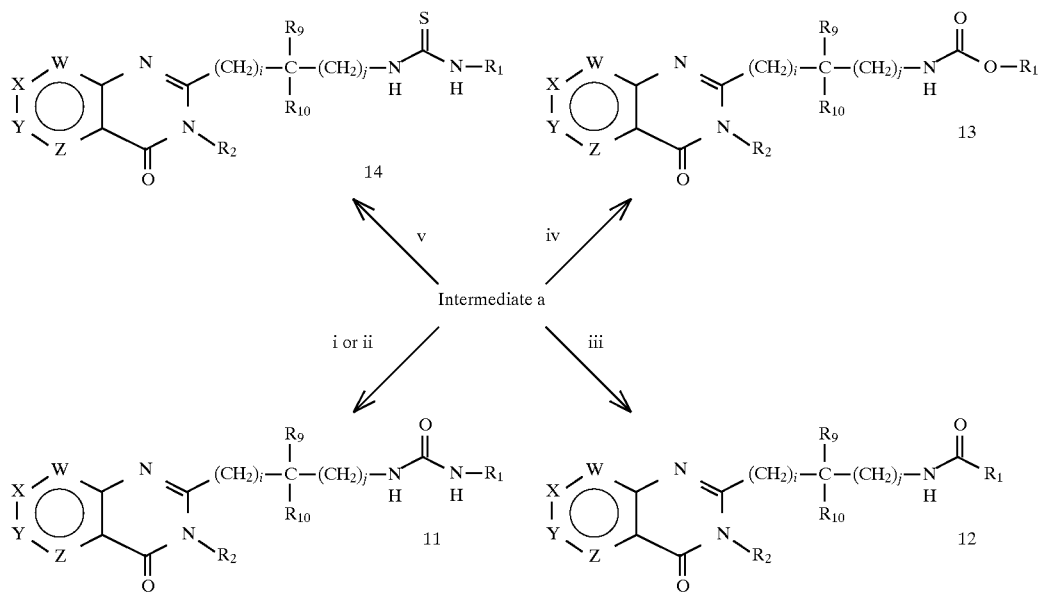
Key:
i) $R_1NCO$
ii) CDI, $R_1-NH_2$
iii) $R_1COCl$, TEA
iv) $R_1OCOCl$, TEA
v) $R_1NCS$
Scheme IV
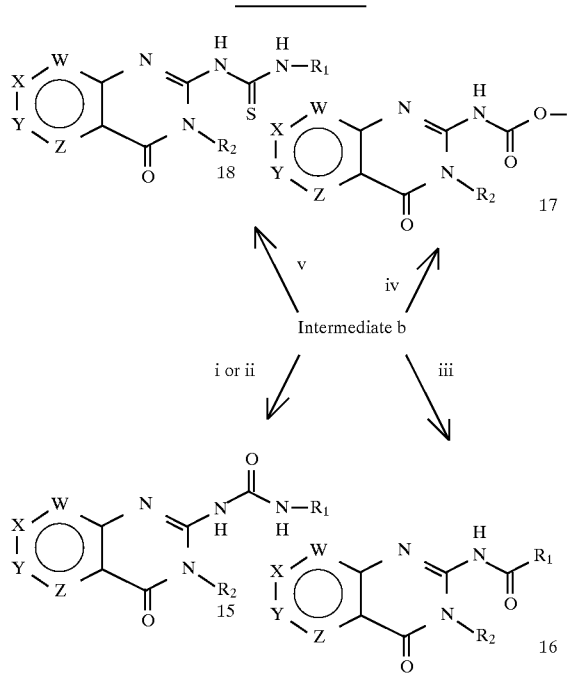
Key:
i) $R_1NCO$
ii) CDI, $R_1-NH_2$
iii) $R_1COCl$, TEA
iv) $R_1OCOCl$, TEA
v) $R_1NCS$
SCHEME IVA
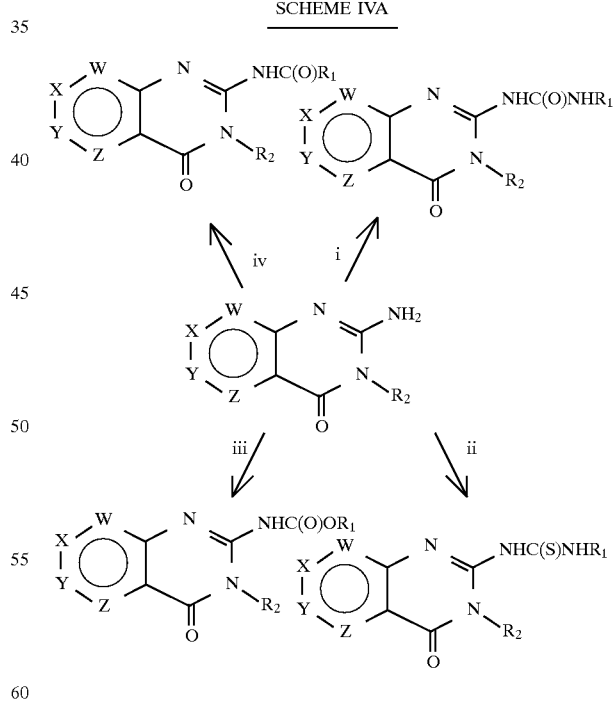
Key:
i) NaH, $R_1NCO$
ii) NaH, $R_1NCS$
iii) NaH, $R_1OCOCl$
iv) NaH, $R_1COCl$ 33
Scheme V
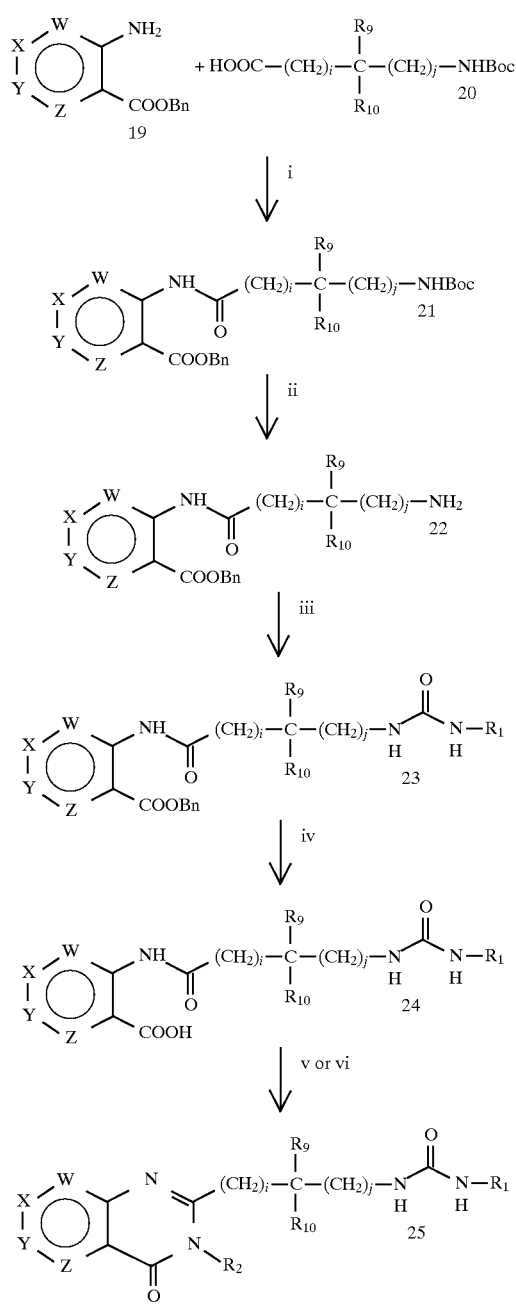
Key:
i) CDI, THF, reflux
ii) HCl
iii) R₁NCO
iv) 10% Pd/C, H₂
v) R₂—NH₂, CDI, THF, reflux
vi) R₂—NH₂, CDI, THF, and then PPTs, reflux
34
Scheme VI
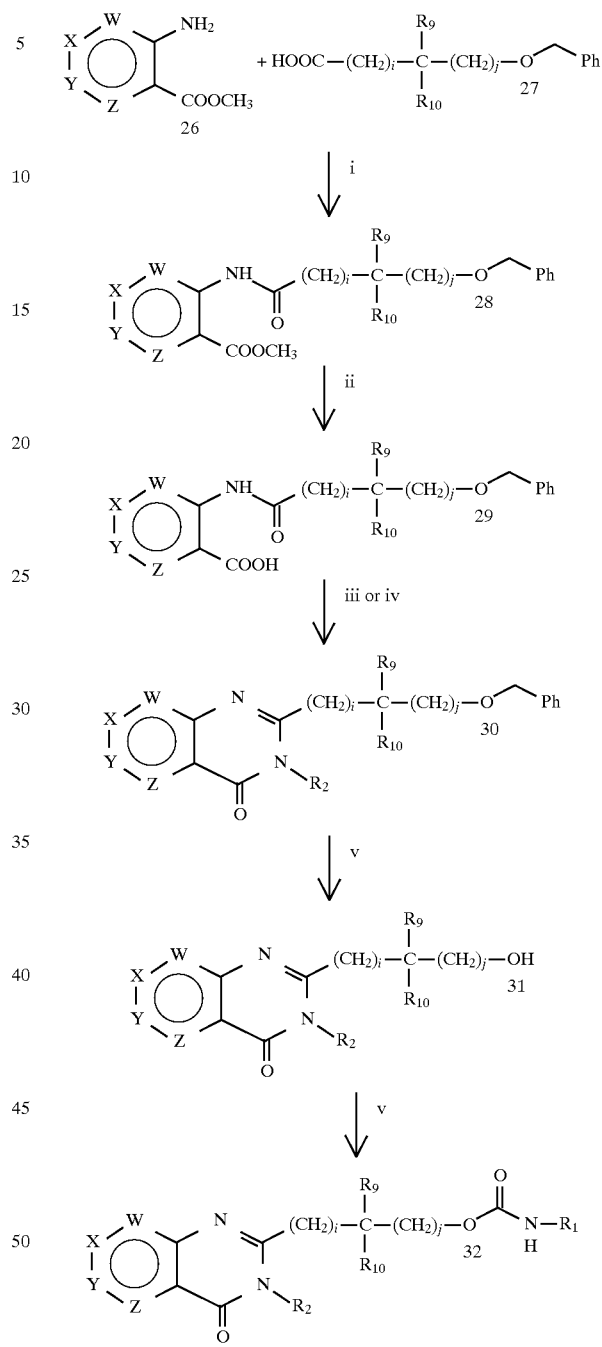
Key:
i) CDI, THF
ii) LiOH, dioxane-water
iii) R₂—NH₂, CDI, THF, reflux
iv) R₂—NH₂, CDI, THF, then PPTs
v) Pd/C, H₂
vi) R₁NCO Scheme VII
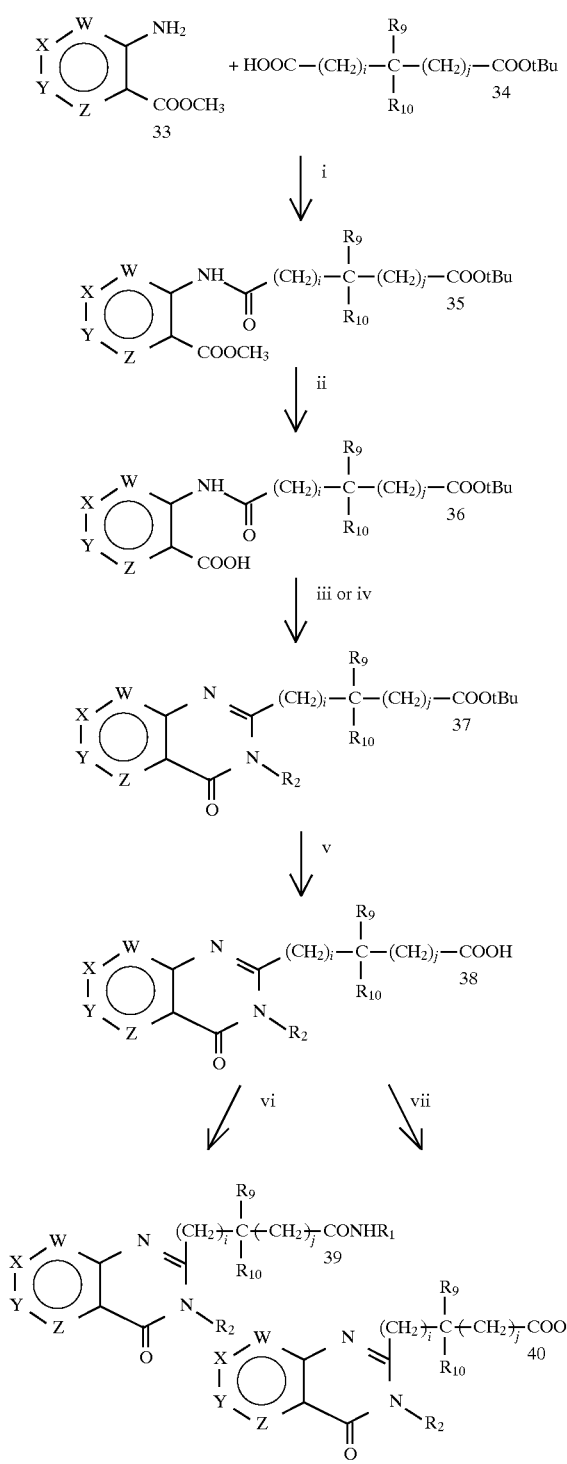
Scheme VIII
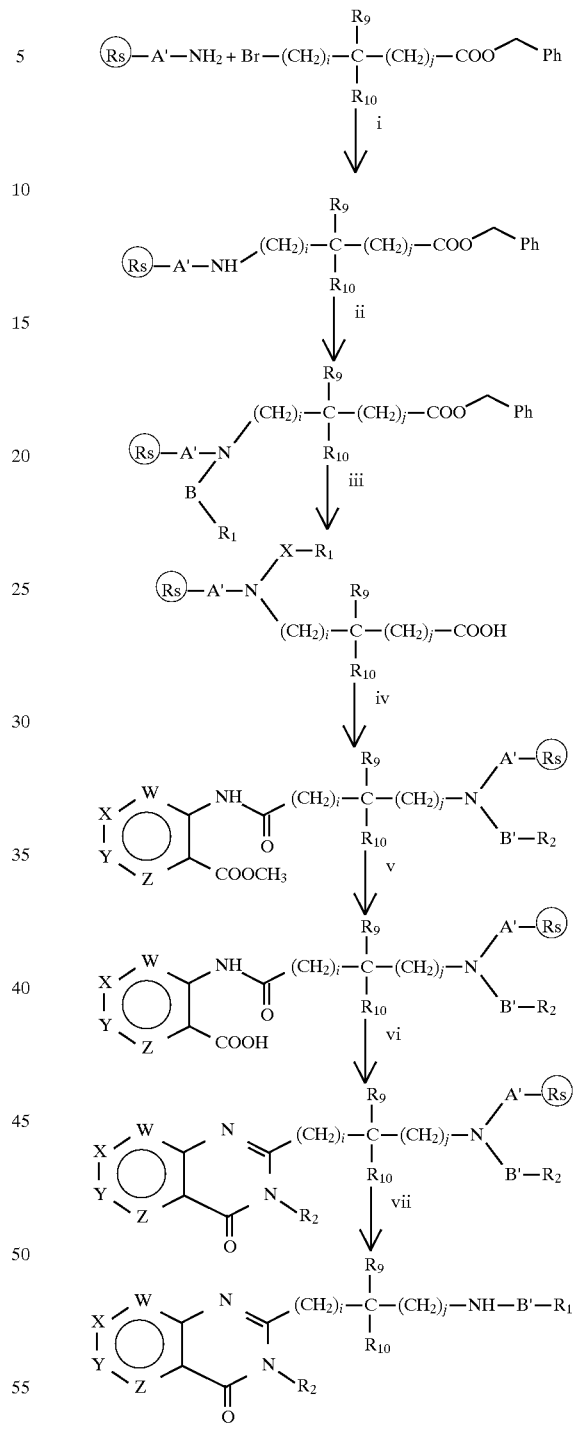
Key:
i) CDI, THF, reflux
ii) LiOH, dioxane-water
iii) $R_2-NH_2$, CDI, THF, reflux
iv) $R_2-NH_2$, CDI, THF, then PPTs
v) HCl
vi) $R_1NH_2$, CDI, THF
vii) $R_1OH$, CDI, THF

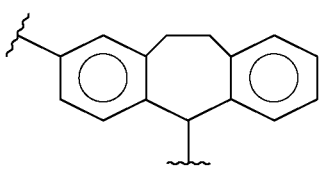

Key:
i) Diisopropylamine, DMF, Δ
ii) R₁COCl, TEA or R₁NCO
    or R₁NCS or R₁OCOCl, TEA
iii) LiOH

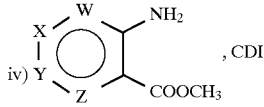, CDI v) LiOH
vi) R₂—NH₂, CDI
vii) TFA
Rs = Polystyrene
B' = —NHCO—
B' = —NHCONH—
B' = —NHCSNH—
B' = —NHCOO—

While the forms of the invention herein disclosed constitute presently preferred embodiments, many others are possible. It is not intended herein to mention all of the possible equivalent forms or ramifications of the invention. It is understood that the terms used herein are merely descriptive rather than limiting and that various changes may be made without departing from the spirit or scope of the invention.

I claim:

1. A process of preparing a 2-amino compound of the structure:

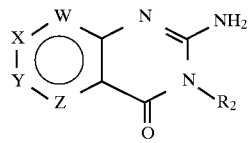

wherein W, X, Y, and Z are each independently selected from C—R₃, C—R₄, C—R₅, C—R₆ and N (nitrogen) and that no more than two of W, X, Y and Z are N;

wherein R₃, R₄, R₅ and R₆ are each independently hydrogen, hydroxy, sulfhydryl, lower alkoxy (1–4 carbon atoms), lower thioalkoxy (1–4 carbon atoms), lower alkyl (1–4 carbon atoms), halo, CN, CF₃, NO₂, COOR₇ or NR₇R₈;

wherein R₇ and R₈ are independently hydrogen or lower alkyl (1–4 carbon atoms);

R₂ is:
an alkyl of 1 to 6 carbon atoms,
unsubstituted, mono- or polysubstituted phenyl or polyaromatic,
unsubstituted, mono- or polysubstituted heteroaromatic with hetero atom(s) N (nitrogen), O (oxygen) and/or S (sulfur), or
unsubstituted, mono- or polysubstituted aralkyl,
unsubstituted, mono- or polysubstituted cyclo or polycycloalkyl hydrocarbon, or
mono- or polyheterocycle (3–8 atoms per ring) with 1 to 4 hetero atoms as N (nitrogen), O (oxygen), or S (sulfur);

wherein substitutions are selected from hydrogen, methyl, methoxy, fluorine, chlorine, bromine, iodine, hydroxy, ethoxy, propoxy, i-propoxy, t-butoxy, ethyl, propyl, i-propyl, trifluoromethyl, 3-cyclopropoxy, thioisopropyl, cyano, N,N-dimethylamino, N,N-dimethylamino methyl, carboxy, carbmethoxy, and tetrazole;

comprising the steps of:
(a) reacting the 2-hydrazine precursor with hydrogen; in presence of a catalyst optionally Raney nickel, and
(b) recovering the 2-amino product.

2. The process of claim 1 wherein the reaction is conducted in the presence of a precious metal catalyst.

3. The process of claim 2 wherein the catalyst is nickel.

4. The process of claim 3 wherein the catalyst is Raney nickel hydride.

5. A process of preparing the 2-amino product of the structure:

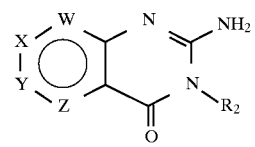

wherein W, X, Y and Z are each independently selected from C—R₃, C—R₄, C—R₅, C—R₆ and N (nitrogen) and that no more than two of W, X, Y, and Z are N;

wherein R₃, R₄, R₅ and R₆ are each independently hydrogen, hydroxy, sulfhydryl, lower alkoxy (1–4 carbon atoms), lower thioalkoxy (1–4 carbon atoms), lower alkyl (1–4 carbon atoms), halo, CN, CF₃, NO₂, COOR₇ or NR₇R₈;

wherein R₇ and R₈ are independently hydrogen or lower alkyl (1–4 carbon atoms);

M is oxygen;

R₂ is:
an alkyl of 1 to 6 carbon atoms,
unsubstituted, mono- or polysubstituted phenyl or polyaromatic,
unsubstituted, mono- or polysubstituted heteroaromatic with hetero atom(s) N (nitrogen), O (oxygen), and/or S (sulfur) or,
unsubstituted, mono- or polysubstituted aralkyl,
unsubstituted, mono- or polysubstituted cyclo or polycycloalkyl hydrocarbon, or
mono- or polyheterocycle (3–8 atoms per ring) with 1 to 4 hetero atoms as N (nitrogen), O (oxygen), or S (sulfur); and wherein substitutions are selected from hydrogen, methyl, methoxy, fluorine, chlorine, bromine, iodine, hydroxy, ethoxy, propoxy, i-propoxy, t-butoxy, ethyl, propyl, i-propyl, trifluoromethyl, 3-cyclopropoxy, thioisopropyl, cyano, N,N-dimethylamino, N,N-dimethylamino methyl, carboxy, carbmethoxy, and tetrazole;

comprising the steps of:
(a) reacting hydrazine with a compound of the structure:

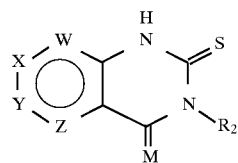

(b) hydrogenating the product of step (a); and
(c) recovering the 2-amino product.

6. The process of claim 5 wherein the product of step (a) has the structure:

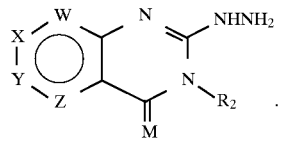

7. A method of producing the compound of Formula I

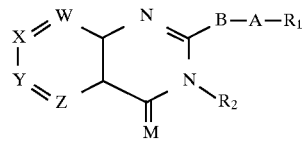  I comprising reacting $R_2NH_2$ with a compound of Formula II:

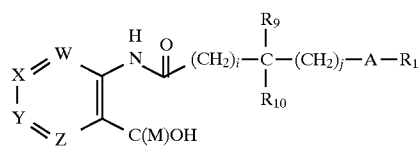  II wherein B is defined as a direct bond or,

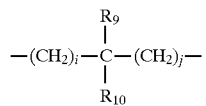

wherein i and j are independently 0 or 1;
$R_9$ and $R_{10}$ are independently hydrogen, lower alkyl (1–4 carbon atoms), or lower alkoxy (1–4 carbon atoms);
A is selected from the group consisting of:

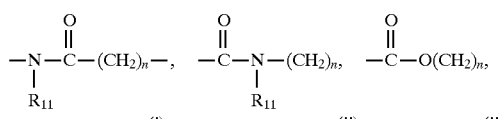

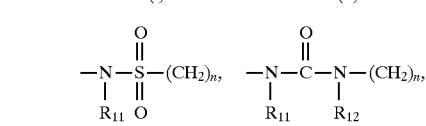

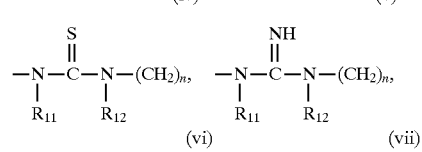

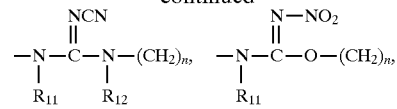

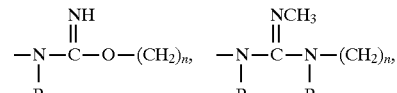

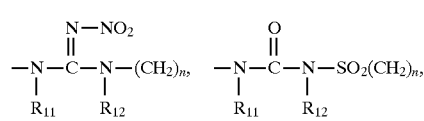

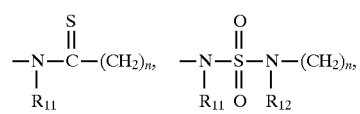

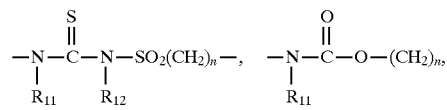

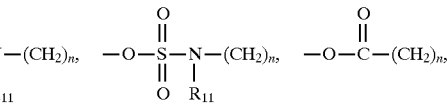

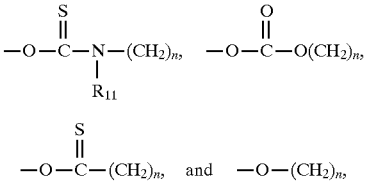

wherein W, X, Y and Z are each independently selected from C—$R_3$, C—$R_4$, C—$R_5$, and N (nitrogen) and that no more than two of W, X, Y, and Z are N;

wherein $R_3$, $R_4$, $R_5$ and $R_6$ are each independently hydrogen, hydroxy, sulfhydryl, lower alkoxy (1–4 carbon atoms), lower thioalkoxy (1–4 carbon atoms), lower alkyl (1–4 carbon atoms), halo, CN, $CF_3$, $NO_2$, $COOR_7$ or $NR_7R_8$;

wherein $R_7$ and $R_8$ are independently hydrogen or lower alkyl (1–4 carbon atoms);

M is oxygen or sulfur;

wherein $R_{11}$ and $R_{12}$ are independently hydrogen or lower alkyl (1–4 carbon atoms); n=0 or 1;

$R_1$ is:
an alkyl of 1 to 6 carbon atoms,
unsubstituted, mono- or polysubstituted phenyl or polyaromatic,
unsubstituted, mono- or polysubstituted heteroaromatic with hetero atom(s) N (nitrogen), O (oxygen), and/or S (sulfur),
unsubstituted, mono- or polysubstituted aralkyl,
unsubstituted, mono- or polysubstituted cyclo or poly-cycloalkyl hydrocarbon, or
mono- or polyheterocycle (3 to 8 atoms per ring) with 1 to 4 hetero atoms selected from the group consisting of N (nitrogen), O (oxygen), and S (sulfur);

wherein the substitutions are selected from hydrogen, methyl, methoxy, fluorine, bromine, chlorine, iodine, trifluoromethyl, cyano, acetyl, carboxy, carbmethoxy, carbethoxy, amino, N,N-dimethylamino, amido, acetyl, methylene carboxy, tetrazole, nitro, cyclohexyl, and adamantyl;

$R_2$ is:
an alkyl of 1 to 6 carbon atoms,
unsubstituted, mono- or polysubstituted phenyl or polyaromatic,
unsubstituted, mono- or polysubstituted heteroaromatic with hetero atom(s) N (nitrogen), O (oxygen), and/or S (sulfur), or
unsubstituted, mono- or polysubstituted cyclo or polycycloalkyl hydrocarbon, or
mono- or polyheterocycle (3–8 atoms per ring) with 1 to 4 hetero atoms selected from the group consisting of N (nitrogen), O (oxygen), and S (sulfur); and
wherein substitutions are selected from hydrogen, methyl, methoxy, fluorine, chlorine bromine, iodine, hydroxy, ethoxy, propoxy, i-propoxy, t-butoxy, ethyl, propyl, i-propyl, trifluoromethyl, 3-cyclopropoxy, thioisopropyl, cyano, N,N-dimethylamino, N,N-dimethylamino methyl, carboxy, carbmethoxy, and tetrazole.

8. The method of claim 1 wherein A is:

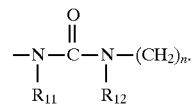

9. The composition of claim 7 wherein A is:

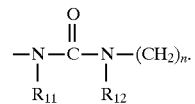

* * * * *